US009381147B2

(12) United States Patent
Fevola et al.

(10) Patent No.: US 9,381,147 B2
(45) Date of Patent: Jul. 5, 2016

(54) COMPOSITIONS COMPRISING ZWITTERIONIC ESTER AMMONIOALKANOATES

(71) Applicant: JOHNSON & JOHNSON CONSUMER INC., Skillman, NJ (US)

(72) Inventors: Michael J. Fevola, Belle Mead, NJ (US); Tobias J. Fuetterer, Princeton, NJ (US); Stacey E. York, Eugene, OR (US); Neil Warren Boaz, Kingsport, TN (US)

(73) Assignee: Johnson & Johnson Consumer Inc., Skillman, NJ (US)

( * ) Notice: Subject to any disclaimer, the term of this patent is extended or adjusted under 35 U.S.C. 154(b) by 0 days.

(21) Appl. No.: 14/518,476

(22) Filed: Oct. 20, 2014

(65) Prior Publication Data

US 2016/0106647 A1 Apr. 21, 2016

(51) Int. Cl.
| *A61Q 5/02* | (2006.01) |
| *C11D 1/62* | (2006.01) |
| *C11D 1/92* | (2006.01) |
| *A61K 8/41* | (2006.01) |
| *A61K 8/49* | (2006.01) |
| *A61K 8/46* | (2006.01) |
| *A61Q 19/10* | (2006.01) |

(52) U.S. Cl.
CPC .............. *A61K 8/416* (2013.01); *A61K 8/466* (2013.01); *A61K 8/4926* (2013.01); *A61Q 5/02* (2013.01); *A61Q 19/10* (2013.01); *A61K 2800/30* (2013.01)

(58) Field of Classification Search
CPC .......... C11D 1/92; C11D 1/62; C11D 3/3927; C11D 3/0094; C11D 3/3915; C11D 3/3917; A61Q 5/02
See application file for complete search history.

(56) References Cited

U.S. PATENT DOCUMENTS

| 2,781,349 | A | 2/1957 | Mannheimer |
| 3,001,997 | A | 9/1961 | Mannheimer |
| 3,280,178 | A | 10/1966 | Barbour |
| 3,280,179 | A | 10/1966 | Ernst |
| 4,259,191 | A | 3/1981 | Wagner |
| 4,687,602 | A | 8/1987 | Ballschuh et al. |
| 5,696,070 | A | 12/1997 | Tachizawa et al. |
| 5,851,982 | A | 12/1998 | Sakata et al. |
| 5,876,705 | A | 3/1999 | Uchiyama et al. |
| 5,972,877 | A | * 10/1999 | Tsuda .................. C11D 1/02 510/137 |
| 7,335,627 | B1 | 2/2008 | O'Lenick et al. |
| 7,375,064 | B1 | 5/2008 | O'Lenick, Jr. |
| 7,507,399 | B1 | 3/2009 | O'Lenick, Jr. |
| 7,667,067 | B1 | 2/2010 | Clendennen et al. |
| 8,889,373 | B2 | 11/2014 | Clendennen |
| 8,900,625 | B2 | 12/2014 | Damaj et al. |
| 9,120,846 | B2 | 9/2015 | Haymore |
| 2007/0042030 | A1 * | 2/2007 | Cevc .................. A61K 9/0019 424/450 |
| 2010/0159393 | A1 | 6/2010 | Fiebag et al. |
| 2011/0300093 | A1 | 12/2011 | Bendejacq et al. |
| 2012/0040395 | A1 | 2/2012 | Clendennen |
| 2012/0277324 | A1 | 11/2012 | Burk et al. |

FOREIGN PATENT DOCUMENTS

| CN | 103468 A | 12/2013 |
| CN | 103468228 | * 12/2013 |
| CN | 103468228 A | 12/2013 |
| DE | 2252687 A1 | 5/1974 |
| DE | 274332 A3 | 12/1989 |
| DE | 278053 A1 | 4/1990 |
| DE | 278054 A1 | 4/1990 |
| DE | 278061 A1 | 4/1990 |
| JP | S4216415 B1 | 9/1967 |
| JP | S4226523 B1 | 12/1967 |
| JP | S56141375 A | 11/1981 |
| JP | 1097065 A | 4/1998 |
| WO | 98/33879 | * 8/1998 |
| WO | WO9833879 A1 | 8/1998 |
| WO | 2007/023336 | * 3/2007 |
| WO | WO2007023336 A2 | 3/2007 |
| WO | WO2007/059021 A1 | 5/2007 |
| WO | WO2009136396 A2 | 11/2009 |
| WO | 2011/114876 | * 9/2011 |
| WO | WO2011114876 A1 | 9/2011 |
| WO | WO2011146595 A2 | 11/2011 |
| WO | WO2012/024233 A2 | 2/2012 |
| WO | WO2012/080018 A2 | 6/2012 |
| WO | WO2012/148739 A1 | 11/2012 |
| WO | WO2013/052087 A1 | 4/2013 |

OTHER PUBLICATIONS

ASTM 1173-07; Standard Test Method for Foaming Properties of Surface-Active Agents.
Chattopadhyay et al.; "Fluorimetric Determination of Critical Micelle Concentration Avoiding Interference from Detergent Charge"; Analytical Biochemistry, vol. 139, pp. 408-412 (1984).
Parris et al.; "Soap Based Detergent Formulation: XXIV. Sulfobetaine Derivatives of Fatty Amides[1]"; Journal of the American Oil Chemists' Society, vol. 54, pp. 294-296 (1977).
Copending U.S. Appl. No. 14/518,505, filed Oct. 20, 2014, Neil Warren Boaz et al.
Copending U.S. Appl. No. 14/518,517, filed Oct. 20, 2014, Neil Warren Boaz et al.
Copending U.S. Appl. No. 14/856,656, filed Sep. 17, 2015, Neil Warren Boaz et al.

(Continued)

*Primary Examiner* — Charles Boyer

(57) ABSTRACT

The present invention provides compositions utilizing a zwitterionic ester ammonioalkanoate surfactant according to Formula 1 and an ingredient selected from the group consisting a surfactant other than said zwitterionic ester ammonioalkanoate surfactant, emulsifiers, conditioning agents, emollients, moisturizers, humectants, thickeners, lubricants, chelating agents, fillers, binding agents, anti-oxidants, preservatives, active ingredients, fragrances, dyes, buffering agents, exfoliates, pH adjusters, inorganic salts, solvents, viscosity controlling agents and opacifying agents, wherein the composition is substantially free of alkylamidoamine and aminoalkylamine.

13 Claims, No Drawings

(56) References Cited

OTHER PUBLICATIONS

Copending U.S. Appl. No. 14/856,830, filed Sep. 17, 2015, Michael J. Fevola et al.

Abele et al., "Cationic and Zwitterionic Polymerizable Surfactants: Quaternary Ammonium Dialkyl Maleates. 1. Synthesis and Characterization", *Langmuir*, Feb. 1, 1999, 15(4):1033-1044.

Gandhi, "Applications of Lipase", *Journal of the American Oil Chemists' Society (JAOCS)*, Springer, DE, Jun. 1, 1997, 74(6):621-634.

Guo et al., "Synthesis of surface-functionalized, probe-containing, polymerized vesicles derived from ammonium bromide surfactants", *Langmuir*, Mar. 1, 1992, 8(3):815-823.

Hashmi et al., "Supramolecular Interaction Controlled Diffusion Mechanism and Improved Mechanical Behavior of Hybrid Hydrogel Systems of Zwitterions and CNT", *Macromolecules*, Dec. 21, 2012, 45(24):9804-9815.

International search report dated Dec. 23, 2015, for corresponding international application PCT/US2015/053426.

Kratzer et al., "A Synethetic Route to Sulfobetaine Methacrylates with Varying Charge Distance", *European Journal of Organic Chemistry*, Dec. 5, 2014, 2014(36):8064-8071.

Liu et al., "Zwitterionic copolymer-based and hydrogen bonding-strengthened self-healing hydrogel", *RSC Advances: An International Journal to Further the Chemical Sciences*, Jan. 1, 2015, 5(42):33083-33088.

Spencer et al., "Zwitterionic Sulfobetaine Inhibitors of Squalene Synthase", *Journal of Organic Chemistry*, Jan. 1, 1999, 64(3):807-818.

Tremblay et al., "One-pot synthesis of polyunsaturated fatty acid amides with antiproliferative properties", *Bioorganic & Medicinal Chemistry Letters*, Nov. 1, 2014, 24(24):5635-5638.

Wu et al., "Stereoisomers of N-substituted soft anticholinergics and their zwitterionic metabolite based on glycopyrrolate—syntheses and pharmacological evaluations", Die Pharmazie, Mar. 2008, 63(3): 200-209.

"Supplementary Examination Guidelines for Determining Compliance with 35 USC 112 and for Treatment of Related issues in patent Application", Fed Reg, vol. 76, No. 27, pp. 7162-7175 and slides 1, 64-67 (2011).

* cited by examiner

COMPOSITIONS COMPRISING ZWITTERIONIC ESTER AMMONIOALKANOATES

PARTIES TO JOINT RESEARCH AGREEMENT

Inventions described or claimed herein were made pursuant to a Joint Research Agreement between Eastman Chemical Company and Johnson & Johnson Consumer & Personal Products Worldwide, a division of Johnson & Johnson Consumer Companies Inc.

FIELD OF INVENTION

The present invention relates to compositions comprising zwitterionic ester ammonioalkanoate surfactants, as defined herein.

BACKGROUND OF THE INVENTION

Cleansing compositions are used to apply to the hair and/or skin of humans in order to provide cleansing of the respective part of the body to be cleaned. With respect to cleansing skin, cleansing formulations are designed to remove dirt, sweat, sebum, and oils from the skin, where cleansing is achieved through the use of conventional surfactants that aid in the uplifting of dirt and solubilization and removal of oily soils from the skin. In addition to removing unwanted materials from the skin, cleansing helps to promote normal exfoliation, and thereby rejuvenates the skin. Conventional detergents, such as cationic, anionic and non-ionic surfactants, are widely used in a variety of cleansing compositions to impart such cleansing properties.

Also, zwitterionic surfactants, like betaines, sultaines and amphoacetates, are widely used in a variety of cleansing compositions. They are best known to generate desirable viscosity, foam and mildness in cleansing formulations, the most commonly used being cocamidopropyl betaine. Other examples include lauramidopropyl betaine, cocamidopropyl hydroxyl sultaine, lauramidopropyl hydroxyl sultaine, sodium lauroamphoacetate, sodium cocoamphoacetate, disodium cocoampho dipropionate and disodium lauroampho dipropionate, and the like. However, these zwitterionic surfactants all bear an amide-moiety and recently have been recognized as possible allergens. In particular, cocamidopropyl betaine is now part of allergy screening tests. Further, allergens and skin irritants such as alkylamidoamines and aminoalkylamines are present in all of the zwitterionic surfactants noted above, the former an intermediate formed during the synthesis of the above zwitterionic surfactants and the latter an unreacted raw material used for the synthesis.

Applicants have recognized the desirability of developing cleansers that are substantially free of zwitterionic surfactants bearing an amide-moiety and possibly alkylamidoamines and aminoalkylamines, while still fulfilling the demand for desirable viscosity, foam and mildness.

Zwitterionic surfactants are best suitable to help generating desirable viscosity, foam and mildness in cleansing formulations. Accordingly, applicants have recognized the need to develop cleansing compositions containing zwitterionic surfactants which do not contain an amide moiety and that are substantially free of alkylamidoamines and aminoalkylamine impurities, and that exhibit desirable viscosity, foam and mildness for consumer use.

SUMMARY OF THE INVENTION

The present invention provides compositions comprising a zwitterionic ester ammonioalkanoate surfactant according to Formula 1, hereinafter referred to as "ZEA surfactants", and an ingredient selected from the group consisting of a surfactant other than the zwitterionic ester ammonioalkanoate surfactant according to Formula 1, emulsifiers, conditioning agents, emollients, moisturizers, humectants, thickeners, lubricants, chelating agents, fillers, binding agents, anti-oxidants, preservatives, active ingredients, fragrances, dyes, buffering agents, exfoliants, pH adjusters, inorganic salts, solvents, viscosity controlling agents and opacifying agents, wherein the composition is substantially free of alkylamidoamine and aminoalkylamine.

DETAILED DESCRIPTION OF THE INVENTION

Applicants have discovered that compositions of the present invention overcome the disadvantages of the prior art and provide compositions that exhibit desirable viscosity and/or foaming action, as compared to the prior art, while maintaining excellent mildness to the skin and eyes. The compositions are substantially free of alkylamidoamine and aminoalkylamine impurities and substantially free of zwitterionic surfactants bearing an amide-moiety. For example, as shown in the Examples, compositions comprising one or more ZEA surfactants tend to exhibit better viscosity building properties, similar or better foaming action, and at least comparable mildness (measured by EpiDerm™ and EpiOcular™ Test) compared to zwitterionic surfactants bearing an amide-moiety and/or containing alkylamidoamine and/or aminoalkylamine impurities, like cocamidopropyl betaine, cocoamphoactetate and cocamidopropyl hydroxy sultaine.

As used herein the term "zwitterionic ester ammonioalkanoate surfactants", or "ZEA surfactants", refers to a zwitterionic surfactant according to Formula 1:

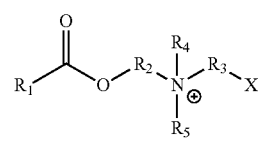

(Formula 1)

where $R_1$ is a linear, branched, saturated or unsaturated C5 to C21 hydrophobe;
$R_2$ is a linear, branched, or cyclic alkyl, hydroxyalkyl, or aromatic group;
$R_3$ is a linear or branched alkyl, hydroxyalkyl, or aromatic group;
$R_4$ is a linear or branched alkyl, hydroxyalkyl, or aromatic group;
$R_5$ is a linear or branched alkyl, hydroxyalkyl, or aromatic group; and
any of $R_2$, $R_4$, or $R_5$ can by linked in a cyclic structure; and
X is —CO2-, —SO3-, or —SO4-.

One specific example of a ZEA surfactant according to Formula 1 is 3-((3-(lauroyloxy)butyl)dimethylammonio)-2-hydroxypropanesulfonate, shown in Formula 2:

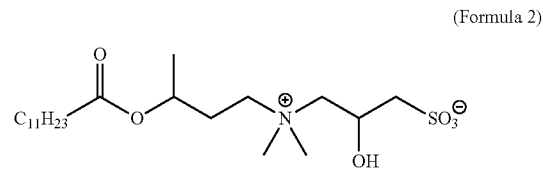

(Formula 2)

An example of a ZEA surfactant according to Formula 1 bearing a cyclic group is 3-(4-lauroyloxy-1-methylpiperidinium-1-yl)-2-hydroxypropanesulfonate, shown in Formula 3,

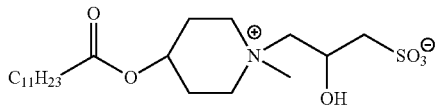

(Formula 3)

where $R_2$ and $R_4$ are linked in a cyclic structure, forming a piperidinium group.

Typically, compositions of the present invention will comprise from about 0.1% to about 30% w/w of ZEA surfactants, or from about 0.5% to about 15% w/w of ZEA surfactants, or from about 1% to about 10% w/w of ZEA surfactants, or from about 1.5% to about 7% w/w of ZEA surfactants, or about 1.5% to about 5% of ZEA surfactants, or about 1.5% to about 3.75% of ZEA surfactants, or about 2.25% to about 3.75% of ZEA surfactants.

As used herein the term "zwitterionic ester ammonioalkanoate sulfonate surfactant" refers to a ZEA surfactant where X is —SO$_3$—.

As used herein the term "zwitterionic ester ammonioalkanoate sulfate surfactant" refers to a ZEA surfactant where X is —SO$_4$—.

Preferably, ZEA surfactants are free of alkylamidoamines and aminoalkylamines They exhibit an ester bond between $R_1$ and $R_2$, whereas the prior art exhibits an amide moiety. Thus, they do not contain amidoamines or aminoalkylamines.

All percentages listed in this specification are percentages by weight, unless otherwise specifically mentioned.

As used herein, the term "substantially free of alkylamidoamine and aminoalkylamine" means a composition that comprises alkylamidoamine and/or aminoalkylamine at maximum levels that mitigate or avoid the detrimental allergic or skin-irritating effects caused by alkylamidoamine and/or aminoalkylamine, for example, less than 0.05% w/w of alkylamidoamine and/or aminoalkylamine. Even more preferable, compositions are free of alkylamidoamine and aminoalkylamine.

Certain embodiments of the present invention may comprise surfactants other than ZEA surfactants. For example, compositions may further comprise anionic, cationic, nonionic and/or zwitterionic surfactants other than ZEA surfactants. In other embodiments, compositions may be substantially free of surfactants other than ZEA surfactants. As used herein, the term "substantially free of surfactant other than ZEA surfactants" means a composition that comprises less than 0.5%, or less than 0.1%, and more preferably less than 0.05% by weight of total surfactant other than ZEA surfactants. Even more preferable, compositions are free of surfactants other than ZEA surfactants. When a surfactant other than the ZEA surfactant is used, the ratio of ZEA surfactant to surfactant other than the ZEA surfactant (w/w) may be from about 0.003 to about 300, or about 0.1 to about 100, or about 0.1 to about 10, or about 0.1 to about 5, or about 0.3 to about 3.

As used herein, the term "anionic surfactant" refers to a surfactant molecule bearing a negative charge and no positive charge. Suitable anionic surfactants include those selected from the following classes of surfactants: alkyl sulfates, alkyl ether sulfates, alkyl monoglyceryl ether sulfates, alkyl sulfonates, alkylaryl sulfonates, alkyl sulfosuccinates, alkyl ether sulfosuccinates, alkyl sulfosuccinamates, alkyl amidosulfosuccinates, alkyl carboxylates, alkyl amidoethercarboxylates, alkyl succinates, fatty acyl sarcosinates, fatty acyl amino acids, fatty acyl taurates, fatty alkyl sulfoacetates, alkyl phosphates, and mixtures of two or more thereof. In certain embodiments, the compositions of the present invention are substantially free of anionic surfactants, and preferably are free of anionic surfactant.

As used herein, the term "sulfated anionic surfactant" refers to anionic surfactants containing a —SO$_4^-$M$^+$ group, with M$^+$ being absent, or H$^+$ or NH$_4^+$ or Na$^+$ or K$^+$ or other monovalent or multivalent anion. Examples of sulfated anionic surfactants include, but are not limited to, sodium lauryl sulfate and sodium laureth sulfate. In certain embodiments, the compositions of the present invention are substantially free of sulfated anionic surfactant, and preferably are free of sulfated anionic surfactant.

As used herein, the term "nonionic surfactant" refers to a surfactant molecule bearing no electrostatic charge. Any of a variety of nonionic surfactants are suitable for use in the present invention. Examples of suitable nonionic surfactants include, but are not limited to, fatty alcohol acid or amide ethoxylates, monoglyceride ethoxylates, sorbitan ester ethoxylates alkyl polyglycosides, mixtures thereof, and the like. Certain preferred nonionic surfactants include polyethyleneoxy derivatives of polyol esters, wherein the polyethyleneoxy derivative of polyol ester (1) is derived from (a) a fatty acid containing from about 8 to about 22, and preferably from about 10 to about 14 carbon atoms, and (b) a polyol selected from sorbitol, sorbitan, glucose, α-methyl glucoside, polyglucose having an average of about 1 to about 3 glucose residues per molecule, glycerine, pentaerythritol and mixtures thereof, (2) contains an average of from about 10 to about 120, and preferably about 20 to about 80 ethyleneoxy units; and (3) has an average of about 1 to about 3 fatty acid residues per mole of polyethyleneoxy derivative of polyol ester. Examples of such preferred polyethyleneoxy derivatives of polyol esters include, but are not limited to PEG-80 sorbitan laurate and Polysorbate 20. PEG-80 sorbitan laurate is a sorbitan monoester of lauric acid ethoxylated with an average of about 80 moles of ethylene oxide. Polysorbate 20 is the laurate monoester of a mixture of sorbitol and sorbitol anhydrides condensed with approximately 20 moles of ethylene oxide.

Another class of suitable nonionic surfactants includes long chain alkyl glucosides or polyglucosides, which are the condensation products of (a) a long chain alcohol containing from about 6 to about 22, and preferably from about 8 to about 14 carbon atoms, with (b) glucose or a glucose-containing polymer. Preferred alkyl gluocosides comprise from about 1 to about 6 glucose residues per molecule of alkyl glucoside. A preferred glucoside is decyl glucoside, which is the condensation product of decyl alcohol with a glucose oligomer Another class of suitable nonionic surfactants includes alkanolamides, like cocamide MEA and cocamide DEA.

As used herein, "zwitterionic surfactant other than a ZEA surfactant" refers to an amphiphilic molecule comprising a hydrophobic group and one or more hydrophilic groups comprising two moieties of opposite formal charges, or capable of bearing opposite formal charges (as a function of acid-base properties and solution pH). Sometimes such surfactants are also referred to as "amphoteric surfactants". Examples of zwitterionic surfactants other than a ZEA surfactant include:

Alkylamidoalkyl betaines of the formula:

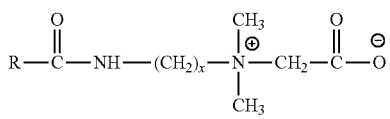

where RCO=$C_6$-$C_{24}$ acyl (saturated or unsaturated) or mixtures thereof and x=1-4. Examples include cocamidoethyl betaine (RCO=coco acyl, x=2), cocamidopropyl betaine (RCO=coco acyl, x=3), lauramidopropyl betaine (RCO=lauroyl, and x=3), myristamidopropyl betaine (RCO=myristoyl, and x=3), soyamidopropyl betaine (R=soy acyl, x=3), and oleamidopropyl betaine (RCO=oleoyl, and x=3).

Alkylamidoalkyl hydroxysultaines of the formula:

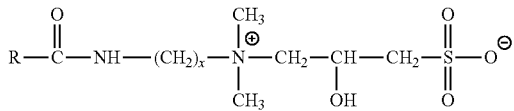

where RCO=$C_6$-$C_{24}$ acyl (saturated or unsaturated) or mixtures thereof. Examples include cocamidopropyl hydroxysultaine (RCO=coco acyl, x=3), lauramidopropyl hydroxysultaine (RCO=lauroyl, and x=3), myristamidopropyl hydroxysultaine (RCO=myristoyl, and x=3), and oleamidopropyl hydroxysultaine (RCO=oleoyl, and x=3).

Alkylamidoalkyl sultaines of the formula:

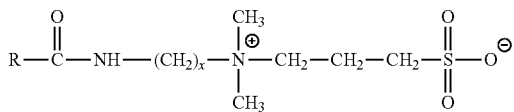

where RCO=$C_6$-$C_{24}$ acyl (saturated or unsaturated) or mixtures thereof. Examples include cocamidopropyl sultaine (RCO=coco acyl, x=3), lauramidopropyl sultaine (RCO=lauroyl, and x=3), myristamidopropyl sultaine (RCO=myristoyl, and x=3), soyamidopropyl betaine (RCO=soy acyl, x=3), and oleamidopropyl betaine (RCO=oleoyl, and x=3).

Amphoacetates of the formula:

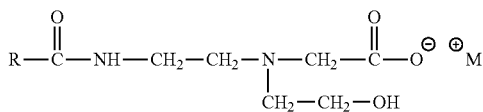

where RCO=$C_6$-$C_{24}$ acyl (saturated or unsaturated) or mixtures thereof and $M^+$=monovalent cation. Examples include sodium lauroamphoacetate (RCO=lauroyl and $M^+$=$Na^+$) and sodium cocoamphoacetate (RCO=coco acyl and $M^+$=$Na^+$).

Amphodiacetates of the formula:

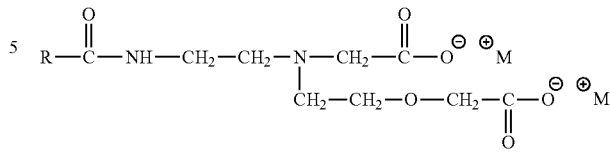

where RCO=$C_6$-$C_{24}$ acyl (saturated or unsaturated) or mixtures thereof and $M^+$=monovalent cation. Examples include disodium lauroamphodiacetate (RCO=lauroyl and M=$Na^+$) and disodium cocoamphodiacetate (RCO=coco acyl and M=$Na^+$).

Amphopropionates of the formula:

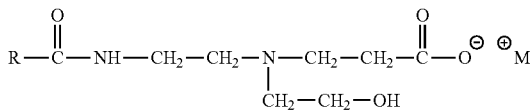

where RCO=$C_6$-$C_{24}$ acyl (saturated or unsaturated) or mixtures thereof and $M^+$=monovalent cation. Examples include sodium lauroamphopropionate (RCO=lauroyl and $M^+$=$Na^+$) and sodium cocoamphopropionate (RCO=coco acyl and $M^+$=$Na^+$).

Amphodipropionates of the formula:

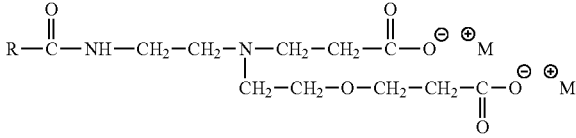

where RCO=$C_6$-$C_{24}$ acyl (saturated or unsaturated) or mixtures thereof and $M^+$=monovalent cation. Examples include disodium lauroamphodipropionate (RCO=lauroyl and $M^+$=$Na^+$) and disodium cocoamphodipropionate (RCO=coco acyl and $M^+$=$Na^+$).

Amphohydroxypropylsulfonates of the formula:

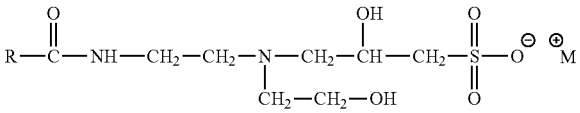

where RCO=$C_6$-$C_{24}$ acyl (saturated or unsaturated) or mixtures thereof and $M^+$=monovalent cation, such as sodium lauroamphohydroxypropylsulfonate (RCO=lauroyl and $M^+$=$Na^+$) and sodium cocoamphohydroxypropylsulfonate (RCO=coco acyl and $M^+$=$Na^+$).

Other examples include amphohydroxyalkylphosphates and alkylamidoalkyl amine oxides.

In certain embodiments of the present invention, the composition may further comprise an inorganic salt. Inorganic salts that are suitable for use in this invention include, but are not limited to, sodium chloride, potassium chloride, sodium bromide, potassium bromide, ammonium chloride, ammonium bromide and other mono-valent as well as multivalent ion containing salts. Typically, compositions of the present invention will comprise from about 0.05% to about 6% w/w of inorganic salt, or from about 0.1% to about 4% w/w of inorganic salt, or from about 0.1% to about 2% w/w of inorganic salt, or from about 0.1% to about 1.5% w/w of inorganic salt.

The pH of composition of the present invention is adjusted to preferably from about 3 to about 9, more preferably from about 3.5 to about 7, and most preferably from about 4 to about 6. The pH of the composition may be adjusted as low as 3 provided that formula stability and performance (e.g. foaming, mildness and viscosity) are not negatively affected. The pH of the composition may be adjusted to the appropriate acidic value using any cosmetically acceptable organic or inorganic acid, such as citric acid, acetic acid, glycolic acid, lactic acid, malic acid, tartaric acid, hydrochloric acid, combinations of two or more thereof or the like.

In certain embodiments of the present invention, the composition may further comprise a cationic surfactant. Classes of cationic surfactants that are suitable for use in this invention include, but are not limited to, alkyl quaternaries (mono, di, or tri), benzyl quaternaries, ester quaternaries, ethoxylated quaternaries, alkyl amines, and mixtures thereof, wherein the alkyl group has from about 6 carbon atoms to about 30 carbon atoms, with about 8 to about 22 carbon atoms being preferred.

In certain embodiments of the present invention, the composition comprises cationic conditioning polymers. Examples of suitable cationic conditioning polymers include cationic cellulose and its derivatives; cationic guar and its derivatives; and diallyldimethylammonium chloride. The cationic cellulose derivative may be a polymeric quaternary ammonium salt derived from the reaction of hydroxyethyl cellulose with a trimethylammonium substituted epoxide, known as Polyquaternium-10. The cationic guar derivative may be a guar hydroxypropyltrimonium chloride. Other useful cationic conditioning polymers are those derived from the monomer diallyldimethylammonium chloride. The homopolymer of this monomer is Polyquatemium-6. The copolymer of diallyldimethylammonium chloride with acrylamide is known as Polyquatemium-7. Other suitable conditioning polymers include those disclosed in U.S. Pat. No. 5,876,705, which is incorporated herein by reference.

The composition of this invention may further contain any other ingredients or additives typically used in personal care products, e.g., dermatological or in cosmetic formulations, including active ingredients. Examples of further ingredients or additives are surfactants, emulsifiers, conditioning agents, emollients, moisturizers, humectants, thickeners, lubricants, chelating agents, fillers, binding agents, anti-oxidants, preservatives, active ingredients, fragrances, dyes, buffering agents, exfoliates, pH adjusters, solvents, viscosity controlling agents and opacifying agents, and the like, provided that they are physically and chemically compatible with the other components of the composition. Active ingredients may include, without limitation, anti-inflammatory agents, anti-bacterials, anti-fungals, anti-itching agents, moisturizing agents, plant extracts, vitamins, and the like. Also included are sunscreen actives which may be inorganic or organic in nature. Of particular interest are any active ingredients suited for topical application of personal care compositions.

The following examples are meant to illustrate the present invention, not to limit it thereto.

EXAMPLES

Test methods used in the Examples are described as follows:

Zero-Shear Viscosity Test:

Determinations of zero-shear apparent viscosity of the cleansing compositions were conducted on a controlled-stress rheometer (AR-2000, TA Instruments Ltd., New Castle, Del., USA). Steady-state shear stress sweeps were performed at 25.0±0.1° C. using a cone-plate geometry. Data acquisition and analysis were performed with the Rheology Advantage software v4.1.10 (TA Instruments Ltd., New Castle, Del., USA). Zero-shear apparent viscosities for Newtonian fluids are reported as the average of viscosity values obtained over a range of shear stresses (0.02-1.0 Pa). For pseudoplastic (shear-thinning) fluids, zero-shear apparent viscosities were calculated via the fitting of shear stress sweep data to an Ellis viscosity model. Except otherwise stated, viscosities are given in CentiPoise (cps).

Formulation Foam Test:

The following Formulation Foam Test was performed on various cleansing compositions to determine the foam volume upon agitation according to the present invention. First, a solution of the test composition is prepared in simulated tap water. To represent the hardness of tap water, 0.455 g of calcium chloride dihydrate (Sigma-Aldrich) is dissolved per 1000 g of DI water, and mixed for 15 minutes prior to use. One (1.0) or five (5.0) grams of test composition is weighed, and this solution is added to 1000 g and mixed until homogeneous for 15 minutes prior to use. To determine the Formulation Foam Volume, the test composition (1000 mL) was added to the sample tank of a SITA R-2000 foam tester (commercially available from Future Digital Scientific, Co.; Bethpage, N.Y.). The test parameters were set to repeat three runs (series count=3) of 250 ml sample size (fill volume=250 ml) with thirteen stir cycles (stir count=13) for a 15 second stir time per cycle (stir time=15 seconds) with the rotor spinning at 1200 RPM (revolution=1200) at a temperature setting of 30° C.±2° C. Foam volume data was collected at the end of each stir cycle and the average and standard deviation of the three runs was determined. The Maximum Foam Volume was reported for each Example as the value after the thirteenth stir cycle.

EpiDerm™ Test:

Upon receipt of the EpiDerm™ Skin Kit (MatTek Corporation), the solutions were stored as indicated by the manufacturer. The EpiDerm™ tissues were stored at 2-8° C. until use. On the day of dosing, EpiDerm™ Assay Medium was warmed to approximately 37° C. Nine-tenths mL of Assay Medium were aliquotted into the appropriate wells of 6-well plates. The 6-well plates were labeled to indicate test article and exposure time. Each EpiDerm™ tissue was inspected for air bubbles between the agarose gel and cell culture insert prior to opening the sealed package. Tissues with air bubbles covering greater than 50% of the cell culture insert area were not used. The 24-well shipping containers were removed from the plastic bag and their surfaces were disinfected with 70% ethanol.

The EpiDerm™ tissues were transferred aseptically into the 6-well plates. The EpiDerm™ tissues were then incubated at 37±1° C. in a humidified atmosphere of 5±1% CO2 in air (standard culture conditions) for at least one hour. The medium was aspirated and 0.9 mL of fresh Assay Medium were added to each assay well below the EpiDerm™ tissues. The plates were returned to the incubator until treatment was initiated. Upon opening the bag, any remaining unused tissues were briefly gassed with an atmosphere of 5% CO2/95% air and placed back at 2-8° C. for later use. The test articles were administered to the test system as 10% w/v dilutions in sterile, deionized water. Each test article dilution was prepared by weighing approximately 1,000 mg of the test article into a pre-labeled conical tube. Sterile, deionized water was added until a 10% w/v dilution was achieved and the tube was vortexed for approximately 1 minute prior to application. In the following, each test article dilution is referred to as the test article.

The test articles were tested in duplicate EpiDerm™ tissues at four exposure times of 4, 8, 16, and 24 hours. One hundred microliters of each test article were applied to each EpiDerm™ tissue. The negative control, 100 μL of sterile, deionized water, was treated in duplicate tissues for 1, 4, 16, and 24 hours. The positive control, 100 μL of 1% Triton®-X-100 (Fisher), was treated in duplicate tissues for 4 and 8 hours. The treated tissues were then incubated at standard culture conditions for the appropriate exposure time. Two sets of dilutions were prepared for the study: one set for the 4, 8, and 24 hours treatment and one set for the 16 hours treatment. A 1.0 mg/mL solution of MTT in warm MTT Addition Medium was prepared no more than 2 hours before use. After the appropriate exposure time, the EpiDerm™ tissues were extensively rinsed with Calcium and Magnesium-Free Dulbecco's Phosphate Buffered Saline ($Ca^{2+}Mg^{2+}$-Free DPBS) and the wash medium was decanted. Three-tenths mL of MTT reagent were added to designated wells in a prelabeled 24-well plate. The EpiDerm™ tissues were transferred to the appropriate wells after rinsing. The plates were incubated for approximately three hours at standard culture conditions. After the incubation period with MTT solution, the EpiDerm™ tissues were blotted on absorbent paper, cleared of excess liquid, and transferred to a prelabeled 24-well plate containing 2.0 mL of isopropanol in each designated well. The plates were covered with parafilm and stored in the refrigerator (2-8° C.) until the last exposure time was harvested. Then the plates were shaken for at least two hours at room temperature. At the end of the extraction period, the liquid within the cell culture inserts was decanted into the well from which the cell culture insert was taken. The extract solution was mixed and 200 μL were transferred to the appropriate wells of a 96-well plate. Two hundred μL of isopropanol were placed in the two wells designated as the blanks. The absorbance at 550 nm ($OD_{550}$) of each well was measured with a Molecular Devices' Vmax plate reader.

The raw absorbance values were captured. The mean $OD_{550}$ value of the blank wells was calculated. The corrected mean $OD_{550}$ value of the negative control(s) was determined by subtracting the mean $OD_{550}$ value of the blank wells from their mean $OD_{550}$ values. The corrected $OD_{550}$ value of the individual test article exposure times and the positive control exposure times was determined by subtracting the mean $OD_{550}$ value of the blank wells from their $OD_{550}$ values.

Corr. test article exposure time $OD_{550}$=Test article exposure time $OD_{550}$–Blank mean $OD_{550}$ The following percent of control calculations were made:

$$\% \text{ Viability} = \frac{\text{Final corrected } OD_{550} \text{ of Test Article or Positive Control}}{\text{corrected mean } OD_{550} \text{ of Negative Control}} \times 100$$

The individual % of control values were then averaged to calculate the mean % of control per exposure time. Test article and positive control viability calculations were performed by comparing the corrected $OD_{550}$ values of each test article or positive control exposure time to a relevant negative control.

Exposure time response curves were plotted with the % of Control on the ordinate and the test article or positive control exposure time on the abscissa. The $ET_{50}$ value was interpolated from each plot. To determine the $ET_{50}$, the two consecutive points were selected, where one exposure time resulted in a relative survival greater than 50%, and one exposure time resulted in less than 50% survival. The two select exposures were used to determine the slope and the y-intercept for the equation y=m(x)+b. Finally, to determine the $ET_{50}$, the equation was solved for y=50. If all of the exposure times showed greater than 50% survival, the $ET_{50}$ value was presented as greater than the maximum exposure time.

EpiOcular™ Test:

Upon receipt of the EpiOcular™ Human Cell Construct Kit (MatTek Corporation), the solutions were stored as indicated by the manufacturer. The EpiOcular™ human cell constructs were stored at 2-8° C. until used. On the day of dosing, EpiOcular™ Assay Medium was warmed to approximately 37° C. Nine-tenths mL of Assay Medium were aliquoted into the appropriate wells of 6-well plates. The six-well plates were labeled to indicate test article and exposure time. The constructs were inspected for air bubbles between the agarose gel and cell culture insert prior to opening the sealed package. Cultures with air bubbles covering greater than 50% of the cell culture area were not used. The 24-well shipping containers were removed from the plastic bag and their surfaces were disinfected with 70% ethanol. The EpiOcular™ human cell constructs were transferred aseptically into the 6-well plates. The constructs were then incubated at 37±1° C. in a humidified atmosphere of 5±1% $CO_2$ in air (standard culture conditions) for at least one hour. The medium was then aspirated and 0.9 mL of fresh Assay Medium were added to each assay well below the EpiOcular™ human cell construct. The plates were returned to the incubator until treatment was initiated.

The test articles were administered to the test system as 3% w/v dilutions in sterile, deionized water (positive and negative control, 1.0% Triton®-X-100 and Johnson's Baby Shampoo, respectively, were administered to the test system as 10% w/v dilutions in sterile, deionized water). Each test article dilution was prepared by weighing the test article into a prelabeled conical tube. Sterile, deionized water was added until a 3% w/v or 10% w/v dilution was achieved and the tube was vortexed prior to application. For the remainder of this report, each test article dilution is referred to as the test article.

The EpiOcular™ cultures were treated in duplicate with the test articles at specific exposure times (from 0.33 up to 16 hours, four time points each). One hundred microliters of each test article were applied to each EpiOcular™ human cell construct. Duplicate cultures of the negative control (exposure time control), 100 μL of sterile, deionized water (Quality Biological), were exposed for 0.25, 4, 8, and 24 hours. Duplicate cultures of the positive control, 100 μL of 0.3% Triton®-X-100 (Fisher), were exposed for 15 and 45 minutes. The exposed cultures were then incubated for the appropriate amount of time at standard culture conditions. After the appropriate exposure time, the EpiOcular™ cultures were extensively rinsed with Calcium and Magnesium-Free Dulbecco's Phosphate Buffered Saline (Ca++Mg++Free-DPBS) and the wash medium was decanted. After rinsing, the tissue was transferred to 5 mL of Assay Medium for a 10 to 20 minute soak at room temperature to remove any test article absorbed into the tissue. A 1.0 mg/mL solution of MTT in warm MTT Addition Medium was prepared no more than 2 hours before use. Three-tenths mL of MTT solution were added to designated wells in a prelabeled 24-well plate. The EpiOcular™ constructs were transferred to the appropriate wells after rinsing with Ca++Mg++Free-DPBS. The trays were incubated for approximately three hours at standard culture conditions. After the incubation period with MTT solution, the EpiOcular™ cultures were blotted on absorbent paper, cleared of excess liquid, and transferred to a prelabeled 24-well plate containing 2.0 mL of isopropanol in each designated well. The plates were sealed with parafilm and stored in the refrigerator (2-8° C.) until the last exposure time was harvested. The plates were then shaken for at least two hours at room temperature. At the end of the extraction period, the liquid within the cell culture inserts was decanted into the well from which the cell culture insert was taken. The extract solution was mixed and 200 µL were transferred to the appropriate wells of a 96-well plate. Two hundred microliters of isopropanol were added to the two wells designated as the blanks. The absorbance at 550 nm ($OD_{550}$) of each well was measured with a Molecular Devices Vmax plate reader.

The raw absorbance values were captured. The mean $OD_{550}$ value of the blank wells was calculated. The corrected mean $OD_{550}$ values of the negative controls were determined by subtracting the mean $OD_{550}$ value of the blank wells from their mean $OD_{550}$ values. The corrected $OD_{550}$ values of the individual test article exposure times and the positive control exposure times were determined by subtracting the mean $OD_{550}$ value of the blank wells from their $OD_{550}$ values. All calculations were performed using an Excel spreadsheet. The following percent of control calculations were made:

$$\% \text{ of Control} = \frac{\text{corrected } OD_{550} \text{ of Test Article or Positive Exposure Time}}{\text{appropriate corrected mean } OD_{550} \text{ Negative Control}} \times 100$$

Exposure time response curves were plotted with the % of Control on the ordinate and the test article or positive control exposure time on the abscissa. The $ET_{50}$ value was interpolated from each plot. To determine the $ET_{50}$, two consecutive points were selected, where one exposure time resulted in a relative survival greater than 50%, and one exposure time resulted in less than 50% survival. Two select points were used to determine the slope and the y-intercept for the equation $y=m(x)+b$. Finally, to determine the $ET_{50}$, the equation was solved for $y=50$. When all of the exposure time points showed greater than 50% survival, the $ET_{50}$ value was presented as greater than the longest test article exposure time ZEA Surfactants (E1-E4) Used in Inventive Compositions and Zwitterionic Surfactants Other than ZEA Surfactants (C1-C4) Used in Comparative Compositions:

Cocamidopropyl betaine, Comparative Examples 1 and 4, were obtained from Evonic Inc. as Tego betaine L7V and Tego betaine F-50, respectively. Sodium lauroamphoacetate, Comparative Example 2, was obtained from Solvay Inc. as Miranol HMD. Cocamidopropyl hydroxyl sultaine, Comparative Example 3, was obtained from Solvay Inc. as Mirataine CBS.

Table 1 lists the zwitterionic ester ammonioalkanoate surfactants according to Formula 1 used for Inventive Example Compositions and zwitterionic surfactants used in Comparative Compositions.

TABLE 1

| INCI or Chemical Name | Trade Name | Activity (%)* |
|---|---|---|
| E1 | 3-((3-(lauroyloxy)propyl)dimethyl-ammonio)-2-hydroxypropanesulfonate | N/A | 28.1* |
| E2 | 3-(4-lauroyloxy-1-methylpiperidinium-1-yl)-2-hydroxypropanesulfonate | N/A | 88.6** |
| E3 | 3-lauroyloxymethyl-1-methyl-piperidinium-1-yl acetate | N/A | 24.4* |
| E4 | 3-((3-(lauroyloxy)butyl)dimethyl-ammonio)-2-hydroxypropanesulfonate | N/A | 29.7* |
| C1 | Cocamidopropyl betaine | Tego ® betaine L7V | 30* |
| C2 | Sodium Lauroamphoacetate | Miranol ® HMD | 27.5* |
| C3 | Cocamidopropyl hydroxyl sultaine | Mirataine ® CBS | 42* |
| C4 | Cocamidopropyl betaine | Tego ® betaine F50 | 38* |

*Activity in water. The aqueous phase may also contain some amounts of sodium chloride and impurities, such as lauric acid.
** E2 was used as a solid also containing sodium chloride and lauric acid.

The ZEA surfactants, E1-E4, noted in Table 1, were prepared as follows:

The schematic process comprises:

(a) contacting an acid or ester or a mixture of acids or esters of Formula 4 with a dialkylamino-alcohol of Formula 5:

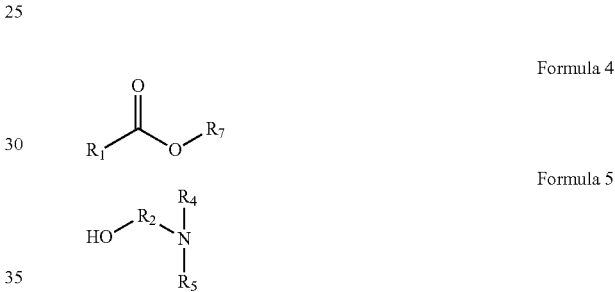

in the presence of an enzyme at conditions effective to form an intermediate of Formula 6:

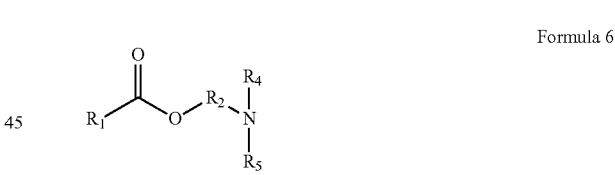

wherein $R_1$, $R_2$, $R_4$, and $R_5$ are as defined above in Formula 1 and $R_7$ is hydrogen or $C_1$-$C_6$ alkyl; and (b) contacting the intermediate of Formula 6 with a alkylating agent at conditions effective to form the ZEA surfactant of Formula 1. Suitable alkylating agents are, for example, 2-chloro acetic acid or 2-hydroxy-3-chloro-propansulfonate.

As a specific example, the preparation of 3-(lauryloxybutyldimethylammonio)-2-hydroxypropanesulfonate is described:

Step a) Intermediate: 3-dimethylaminopropyl laurate

To a 50-mL conical bottom plastic vial was added methyl laurate (38.5 mmol), dimethylaminobutanol (46.2 mmol, 1.2 eq), and Novozym 435 (400 mg). A syringe was inserted through the cap and two additional holes were punched for gas to exit. Nitrogen was bubbled at a rate sufficient to mix the contents. The vial was placed in a heating block set to 65° C. The reaction was monitored by GC/MS to observe the disappearance of starting material. The reaction was complete after approximately 24 hours. The reaction mixture was allowed to cool. The Novozym 435 was removed by filtration to afford the product as a pale, yellow oil (9.2 g; 67% yield) without further purification.

Step b) Final Product: 3-(lauryloxypropyldimethylammonio)-2-hydroxypropanesulfonate To a 250-mL round bottom flask with a magnetic stir bar and a condenser was added 3-dimethylaminobutyl laurate (33.5 mmol), sodium 2-hydroxy-3-chloropropanesulfonate (about 90 wt %; 35.2 mmol, 1.05 equivalents), sodium carbonate (3.35 mmol; 0.10 equivalents), isopropanol (10 mL), and water (10 mL). The reaction mixture was heated in a 90° C. oil bath for 18 hours to afford 99.5 area % conversion according to HPLC analysis. The mixture was concentrated at reduced pressure to 28.31 g. Water (23 g) was added and the mixture was heated to afford solution. The mixture was placed in a 65° C. oil bath, and the headspace was purged with nitrogen (1500 mL/min) for 2 hours to remove residual isopropanol to a weight of 33.78 g. Water (17.5 g) was added and the mixture was stirred at 65° C. for 10 min to afford a homogeneous solution. The total weight of the solution was 52 g, indicating a 30% w/w solution of 3-(lauryloxybutyldimethylammonio)-2-hydroxypropanesulfonate in water. $^1$H NMR analysis was consistent with the product structure.

The following compositions, Inventive Examples (E5-E66) and Comparative Examples (C5-O50) were prepared utilizing different types of formulation ingredients (i.e. raw materials from various suppliers) in addition to the ZEA surfactants. These materials, along with INCI names, trade names and suppliers are listed below:

Anionic surfactants:
  Sodium laureth-2 sulfate was obtained from Solvay Inc. as Rhodapex® ES-2K.
  Ammonium lauryl sulfate was obtained from BASF as Standapol®A.
  Alpha olefin sulfonate was obtained from Stepan as Bioterge®AS 40-CP.
  Sodium cocoyl glutamate was obtained from BASF as Plantapon®ACG H2
  Sodium starch sulfosuccinate was obtained from Akzo Nobel Personal Care as Structure PS-111.
Non-ionic surfactants:
  PEG-80 Sorbitan Laurate was obtained from Croda Inc. as Atlas G-4280.
  PEG-150 Distearate was obtained from Ethox Chemical as Ethox PEG-6000 DS Special.
  Polyglycerol-10 laurate and polyglycerol-10 oleate were obtained from Lonza as Polyaldo® 10-1-L and Polyaldo® 10-1-O, respectively.
Cationic (quaternary) conditioning polymers:
  Polyquaternium-10 was obtained from Dow Chemical as Ucare® JR-400
  Guar hydroxypropyl trimonium chloride was obtained from Solvay Inc. as Jaguar® C17.
Humectants:
  Glycerin was obtained from Emery Oleochemicals as Emery 917.
Chelating Agents:
  Tetrasodium EDTA was obtained from Dow Chemical as Versene™ 100 XL.
Organic Acids/Preservatives:
  Sodium Benzoate, NF, FCC was obtained from Emerald Performance Materials
  Citric acid was obtained from Formosa Laboratories Inc (for DSM) (Taiwan).
Preservatives:
  Phenoxy ethanol and ethylhexylglycerin were obtained from Schülke Inc. as Euxyl® PE 9010.

Inventive Examples E5-E18 and Comparative Examples C5-C14

Preparation and Measurement of Certain Compositions of the Invention with SLES as the Anionic Surfactant and Comparative Compositions Compositions E5-E18 and Comparative Compositions C5-C14 were made in accord with the following procedure: Unless otherwise indicated, all materials were added in amounts such that the compositions contain resulting weight percent amounts of active as indicated for each composition in Tables 2, 3 and 4. For example, 3.75% w/w active of cocamidopropyl betaine (as given in table 2, C5) corresponds to 12.5% w/w Tego betaine L7V, which has an activity of 30% w/w; 3.75% w/w/30% w/w=12.5% w/w.

Preparation of Stock Solutions: Compositions E5-E18 and Comparative Compositions C5-C14 were made using stock solutions, which had been prepared as follows: a) Stock with zwitterionic surfactant: To an appropriately sized vessel equipped with a hotplate and overhead mechanical stirrer, the required amount of DI water (Millipore, Model Direct Q), zwitterionic surfactant, and sodium chloride was added and mixed at 200-350 rpm until the mixture was homogeneous, for C1, E1 and E4 at room temperature, and for E2 at 50° C., respectively. Then, sodium benzoate and citric acid (20% w/w solution in DI water) were added at room temperature to adjust to the desired pH value 4.4-4.6. Water was added in q.s. to 100 wt %, and the batch was allowed to mix until uniform before being discharged to an appropriate storage vessel; b) Stock with anionic surfactant: To an appropriately sized vessel equipped with a hotplate and overhead mechanical stirrer, the required amount of DI water (Millipore, Model Direct Q), anionic surfactant, and citric acid were added and mixed at 200-350 rpm at room temperature until the mixture is homogeneous. An amount of citric acid (as 20% w/w solution in DI water) was added to adjust to the desired pH value 4.4-4.6. Water was added in q.s. to 100% w/w and the batch was allowed to mix until uniform before being discharged to an appropriate storage vessel.

Compositions E5-E18 and Comparative Compositions C5-C14 were made as follows: To an appropriately sized vessel equipped with a hotplate and overhead mechanical stirrer, the required amount of a) stock with zwitterionic surfactant and b) stock with anionic surfactant were added. Water was added in q.s. to 100% w/w. The batch was heated to 50° C. under mixing and mixed at 200-350 rpm for 20 minutes. The batch was allowed to cool to room temperature without mixing.

Tables 2-4 list Inventive Compositions (E5-E18) and Comparative Composition (C5-C14) made from the inventive ZEA surfactants (E1-E4) and comparative zwitterionic surfactants (C and C2).

The Zero Shear Viscosity were measured in accord with the Zero Shear Viscosity Test as described herein. The results are shown in Table 5. As a result, applicants discovered that zwitterionic surfactants according to Formula 1 have the tendency to build higher viscosity in comparison to zwitterionic alkylamidoamine betaine surfactants in compositions containing sodium laureth sulfate as the anionic surfactant.

TABLE 2

| Material | Trade Name | Activity (%) | E5 wt. % | E6 wt. % | E7 wt. % | E8 wt. % | E9 wt. % | E10 wt. % | C5 wt. % | C6 wt. % |
|---|---|---|---|---|---|---|---|---|---|---|
| Weight ratio zwitterionic/amphoteric to anionic surfactant (active to active) | | | 1.63 | 1.63 | 1.63 | 1.63 | 1.63 | 1.63 | 1.63 | 1.63 |
| Zwitterionic (weight % active) | | | | | | | | | | |
| E1 | N/A | 28.1 | 3.75 | 3.75 | | | | | | |
| E2 | N/A | 88.6 | | | 3.75 | 3.75 | | | | |
| E4 | N/A | 29.7 | | | | | 3.75 | 3.75 | | |
| C1 | Tego betaine L7V | 30 | | | | | | | 3.75 | 3.75 |
| Anionic (weight % active) | | | | | | | | | | |
| Sodium laureth-2 Sulfate | Rhodapex ES-2K | 26 | 2.3 | 2.3 | 2.3 | 2.3 | 2.3 | 2.3 | 2.3 | 2.3 |
| Organic acids | | | | | | | | | | |
| Sodium Benzoate | Sodium Benzoate, NF, FCC | 100 | 0.50 | 0.50 | 0.50 | 0.50 | 0.50 | 0.50 | 0.50 | 0.50 |
| Citric Acid | Citric Acid solution | 20 | Q.S. to pH 4.5 | Q.S. to pH 4.5 | Q.S. to pH 4.5 | Q.S. to pH 4.5 | Q.S. to pH 4.5 | Q.S. to pH 4.5 | Q.S. to pH 4.5 | Q.S. to pH 4.5 |
| Other | | | | | | | | | | |
| Sodium Chloride | Sodium Chloride, USP | 100 | 0 | 1.25 | 0 | 1.25 | 0 | 1.25 | 0 | 1.25 |
| Water | Purified water, USP | 100 | Q.S. to 100% | Q.S. to 100% | Q.S. to 100% | Q.S. to 100% | Q.S. to 100% | Q.S. to 100% | Q.S. to 100% | Q.S. to 100% |

TABLE 3

| Material | Trade Name | Activity (%) | E11 wt. % | E12 wt. % | E13 wt. % | E14 wt. % | C7 wt. % | C8 wt. % | C9 wt. % | C10 wt. % |
|---|---|---|---|---|---|---|---|---|---|---|
| Weight ratio zwitterionic/amphoteric to anionic surfactant (active to active) | | | 0.87 | 0.71 | 0.51 | 0.36 | 0.87 | 0.71 | 0.51 | 0.36 |
| Zwitterionic (weight % active) | | | | | | | | | | |
| E4 | N/A | 29.7 | 3.75 | 3.75 | 3.75 | 3.75 | | | | |
| C1 | Tego betaine L7V | 30 | | | | | 3.75 | 3.75 | 3.75 | 3.75 |
| Anionic (weight % active) | | | | | | | | | | |
| Sodium laureth-2 Sulfate | Rhodapex ES-2K | 26 | 4.3 | 5.3 | 7.3 | 10.3 | 4.3 | 5.3 | 7.3 | 10.3 |
| Organic acids | | | | | | | | | | |
| Sodium Benzoate | Sodium Benzoate, NF, FCC | 100 | 0.50 | 0.50 | 0.50 | 0.50 | 0.50 | 0.50 | 0.50 | 0.50 |
| Citric Acid | Citric Acid solution | 20 | Q.S. to pH 4.5 | Q.S. to pH 4.5 | Q.S. to pH 4.5 | Q.S. to pH 4.5 | Q.S. to pH 4.5 | Q.S. to pH 4.5 | Q.S. to pH 4.5 | Q.S. to pH 4.5 |
| Other | | | | | | | | | | |
| Sodium Chloride | Sodium Chloride, USP | 100 | 0.75 | 0.75 | 0.75 | 0.75 | 0.75 | 0.75 | 0.75 | 0.75 |
| Water | Purified water, USP | 100 | Q.S. to 100% | Q.S. to 100% | Q.S. to 100% | Q.S. to 100% | Q.S. to 100% | Q.S. to 100% | Q.S. to 100% | Q.S. to 100% |

TABLE 4

| Material | Trade Name | Activity (%) | E15 wt. % | E16 wt. % | E17 wt. % | E18 wt. % | C11 wt. % | C12 wt. % | C13 wt. % | C14 wt. % |
|---|---|---|---|---|---|---|---|---|---|---|
| Weight ratio zwitterionic/amphoteric to anionic surfactant (active to active) | | | 0.87 | 0.87 | 0.87 | 0.87 | 0.87 | 0.87 | 0.87 | 0.87 |

TABLE 4-continued

| Material | Trade Name | Activity (%) | E15 wt. % | E16 wt. % | E17 wt. % | E18 wt. % | C11 wt. % | C12 wt. % | C13 wt. % | C14 wt. % |
|---|---|---|---|---|---|---|---|---|---|---|
| Zwitterionic (weight % active) | | | | | | | | | | |
| E2 | N/A | 88.6 | 3.75 | 3.75 | | | | | | |
| E4 | N/A | 29.7 | | | 3.75 | 3.75 | | | | |
| C1 | Tego betaine L7V | 30 | | | | | 3.75 | 3.75 | | |
| C2 | Miranol HMD | 27.5 | | | | | | | 3.75 | 3.75 |
| Anionic (weight % active) | | | | | | | | | | |
| Sodium laureth-2 Sulfate | Rhodapex ES-2K | 26 | 4.3 | 4.3 | 4.3 | 4.3 | 4.3 | 4.3 | 4.3 | 4.3 |
| Organic acids | | | | | | | | | | |
| Sodium Benzoate | Sodium Benzoate, NF, FCC | 100 | 0.50 | 0.50 | 0.50 | 0.50 | 0.50 | 0.50 | 0.50 | 0.50 |
| Citric Acid | Citric Acid solution | 20 | Q.S. to pH 4.5 | Q.S. to pH 4.5 | Q.S. to pH 4.5 | Q.S. to pH 4.5 | Q.S. to pH 4.5 | Q.S. to pH 4.5 | Q.S. to pH 4.5 | Q.S. to pH 4.5 |
| Other | | | | | | | | | | |
| Sodium Chloride | Sodium Chloride, USP | 100 | 0 | 0.75 | 0 | 0.75 | 0 | 0.75 | 0 | 0.75 |
| Water | Purified water, USP | 100 | Q.S. to 100% | Q.S. to 100% | Q.S. to 100% | Q.S. to 100% | Q.S. to 100% | Q.S. to 100% | Q.S. to 100% | Q.S. to 100% |

TABLE 5

| Example | Composition Information | Viscosity (Cps) |
|---|---|---|
| E5 | 3.75% w/w zwitterionic surfactant | NA |
| E7 | 2.3% w/w anionic surfactant (SLES) | 1920 |
| E9 | 0% w/w sodium chloride | 67210 |
| C5 | | 1510 |
| E6 | 3.75% w/w zwitterionic surfactant | NA |
| E8 | 2.3% w/w anionic surfactant (SLES) | NA |
| E10 | 1.25% w/w sodium chloride | 552 |
| C6 | | 15600 |
| E11 | 3.75% w/w zwitterionic surfactant | 37620 |
| C7 | 4.3% w/w anionic surfactant (SLES) 0.75% w/w sodium chloride | 6708 |
| E12 | 3.75% w/w zwitterionic surfactant | 116700 |
| C8 | 5.3% w/w anionic surfactant (SLES) 0.75% w/w sodium chloride | 6501 |
| E13 | 3.75% w/w zwitterionic surfactant | 134100 |
| C9 | 7.3% w/w anionic surfactant (SLES) 0.75% w/w sodium chloride | 1384 |
| E14 | 3.75% w/w zwitterionic surfactant | 93650 |
| C10 | 10.3% w/w anionic surfactant (SLES) 0.75% w/w sodium chloride | 2426 |
| E15 | 3.75% w/w zwitterionic surfactant | 38580 |
| E16 | 4.3% w/w anionic surfactant (SLES) | 35120 |
| C11 | 0% w/w sodium chloride | 234 |
| C12 | | 212 |
| E17 | 3.75% w/w zwitterionic surfactant | 2568 |
| E18 | 4.3% w/w anionic surfactant (SLES) | 37620 |
| C13 | 0.75% w/w sodium chloride | 6708 |
| C14 | | 355 |

Inventive Examples E19-E24 and Comparative Examples C15-C16

Preparation and Measurement of Certain Compositions of the Invention with ALS as the Anionic Surfactant and Comparative Compositions Inventive Compositions E19-E24 and Comparative Compositions C15-C16 were made in accord with the procedure described for Compositions E5-E18 and Comparative Compositions C5-C14, except that Standapol A was used as the anionic surfactant instead of Rhodapex ES-2K. Table 6 lists such compositions.

The Zero Shear Viscosity were measured in accord with the Zero Shear Viscosity Test as described herein. The results are shown in Table 7. As a result, applicants discovered that zwitterionic ester ammonioalkanoate surfactants have the tendency to build equivalent or higher viscosity in comparison to zwitterionic alkylamidoamine betaine surfactants in compositions containing ammonium lauryl sulfate as the anionic surfactant, especially at salt concentrations from 0% w/w to around 1% w/w added sodium chloride.

TABLE 6

| Material | Trade Name | Activity (%) | E19 wt. % | E20 wt. % | E21 wt. % | E22 wt. % | E23 wt. % | E24 wt. % | C15 wt. % | C16 wt. % |
|---|---|---|---|---|---|---|---|---|---|---|
| Weight ratio zwitterionic/amphoteric to anionic surfactant (active to active) | | | 0.32 | 0.32 | 0.32 | 0.32 | 0.32 | 0.32 | 0.32 | 0.32 |

TABLE 6-continued

| Material | Trade Name | Activity (%) | E19 wt. % | E20 wt. % | E21 wt. % | E22 wt. % | E23 wt. % | E24 wt. % | C15 wt. % | C16 wt. % |
|---|---|---|---|---|---|---|---|---|---|---|
| Zwitterionic (weight % active) | | | | | | | | | | |
| E1 | N/A | 28.1 | 2.25 | 2.25 | | | | | | |
| E2 | N/A | 88.6 | | | 2.25 | 2.25 | | | | |
| E4 | N/A | 29.7 | | | | | 2.25 | 2.25 | | |
| C1 | Tego betaine L7V | 30 | | | | | | | 2.25 | 2.25 |
| Anionic (weight % active) | | | | | | | | | | |
| Ammonium lauryl Sulfate | Standapol A | 28 | 7 | 10 | 7 | 10 | 7 | 10 | 7 | 10 |
| Organic acids | | | | | | | | | | |
| Sodium Benzoate | Sodium Benzoate, NF, FCC | 100 | 0.50 | 0.50 | 0.50 | 0.50 | 0.50 | 0.50 | 0.50 | 0.50 |
| Citric Acid | Citric Acid solution | 20 | Q.S. to pH 4.5 | Q.S. to pH 4.5 | Q.S. to pH 4.5 | Q.S. to pH 4.5 | Q.S. to pH 4.5 | Q.S. to pH 4.5 | Q.S. to pH 4.5 | Q.S. to pH 4.5 |
| Other | | | | | | | | | | |
| Sodium Chloride | Sodium Chloride, USP | 100 | 0 | 1.25 | 0 | 1.25 | 0 | 1.25 | 0 | 1.25 |
| Water | Purified water, USP | 100 | Q.S. to 100% | Q.S. to 100% | Q.S. to 100% | Q.S. to 100% | Q.S. to 100% | Q.S. to 100% | Q.S. to 100% | Q.S. to 100% |

TABLE 7

| Example | Composition Information | Viscosity (Cps) |
|---|---|---|
| E19 | 2.25% w/w/zwitterionic surfactant | 3183 |
| E21 | 7% w/w/anionic surfactant (ALS) | 18890 |
| E23 | 0% w/w sodium chloride | 83880 |
| C15 | | 118 |
| E20 | 2.25% w/w/zwitterionic surfactant | 2585 |
| E22 | 10% w/w/anionic surfactant (ALS) | 20300 |
| E24 | 1.25% w/w sodium chloride | 909 |
| C16 | | 18920 |

Inventive Examples E25-E30 and Comparative Examples C17-C22

Preparation and Measurement of Certain Compositions of the Invention with AOS as the Anionic Surfactant and Comparative Compositions Compositions E25-E30 and Comparative Compositions C17-C22 were made in accord with the procedure described for Compositions E5-E18 and Comparative Compositions C5-C14, except that Bioterge-AS 40-CP was used as the anionic surfactant instead of Rhodapex ES-2K. Table 8 and 9 list such compositions.

The Zero Shear Viscosity was measured in accord with the Zero Shear Viscosity Test as described herein. The results are shown in Table 10. As a result and surprisingly, applicants discovered that zwitterionic ester ammonioalkanoate surfactants can build viscosity in compositions containing alpha olefin sulfonate as the anionic surfactant, whereas zwitterionic alkylamidoamine betaine surfactants cannot.

TABLE 8

| Material | Trade Name | Activity (%) | E25 wt. % | E26 wt. % | E27 wt. % | C17 wt. % | C18 wt. % | C19 wt. % |
|---|---|---|---|---|---|---|---|---|
| Weight ratio zwitterionic/amphoteric to anionic surfactant (active to active) | | | 1.67 | 1 | 0.51 | 1.67 | 1 | 0.51 |
| Zwitterionic (weight % active) | | | | | | | | |
| E4 | N/A | 29.7 | 3.75 | 3.75 | 3.75 | | | |
| C1 | Tego betaine L7V | 30 | | | | 3.75 | 3.75 | 3.75 |
| Anionic (weight % active) | | | | | | | | |
| Alpha olefin sulfonate | Bioterge-AS 40-CP | 39 | 2.25 | 3.75 | 7.35 | 2.25 | 3.75 | 7.35 |
| Organic acids | | | | | | | | |
| Sodium Benzoate | Sodium Benzoate, NF, FCC | 100 | 0.50 | 0.50 | 0.50 | 0.50 | 0.50 | 0.50 |

TABLE 8-continued

| Material | Trade Name | Activity (%) | E25 wt. % | E26 wt. % | E27 wt. % | C17 wt. % | C18 wt. % | C19 wt. % |
|---|---|---|---|---|---|---|---|---|
| Citric Acid | Citric Acid solution | 20 | Q.S. to pH 4.5 | Q.S. to pH 4.5 | Q.S. to pH 4.5 | Q.S. to pH 4.5 | Q.S. to pH 4.5 | Q.S. to pH 4.5 |
| | | | Other | | | | | |
| Sodium Chloride | Sodium Chloride, USP | 100 | 0.75 | 0.75 | 0.75 | 0.75 | 0.75 | 0.75 |
| Water | Purified water, USP | 100 | Q.S. to 100% | Q.S. to 100% | Q.S. to 100% | Q.S. to 100% | Q.S. to 100% | Q.S. to 100% |

TABLE 9

| Material | Trade Name | Activity (%) | E28 wt. % | E29 wt. % | E30 wt. % | C20 wt. % | C21 wt. % | C22 wt. % |
|---|---|---|---|---|---|---|---|---|
| Weight ratio zwitterionic/amphoteric to anionic surfactant (active to active) | | | 1 | 1 | 1 | 1 | 1 | 1 |
| Zwitterionic (weight % active) | | | | | | | | |
| E2 | N/A | 88.6 | 3.75 | 3.75 | 3.75 | | | |
| C1 | Tego betaine L7V | 30 | | | | 3.75 | 3.75 | 3.75 |
| Anionic (weight % active) | | | | | | | | |
| Alpha olefin sulfonate | Bioterge-AS 40-CP | 39 | 3.75 | 3.75 | 3.75 | 3.75 | 3.75 | 3.75 |
| Organic acids | | | | | | | | |
| Sodium Benzoate | Sodium Benzoate, NF, FCC | 100 | 0.50 | 0.50 | 0.50 | 0.50 | 0.50 | 0.50 |
| Citric Acid | Citric Acid solution | 20 | Q.S. to pH 4.5 | Q.S. to pH 4.5 | Q.S. to pH 4.5 | Q.S. to pH 4.5 | Q.S. to pH 4.5 | Q.S. to pH 4.5 |
| Other | | | | | | | | |
| Sodium Chloride | Sodium Chloride, USP | 100 | 0 | 0.75 | 1.25 | 0 | 0.75 | 1.25 |
| Water | Purified water, USP | 100 | Q.S. to 100% | Q.S. to 100% | Q.S. to 100% | Q.S. to 100% | Q.S. to 100% | Q.S. to 100% |

TABLE 10

| Example | Composition Information | Viscosity (Cps) |
|---|---|---|
| E25 | 3.75% w/w/zwitterionic surfactant | 1656 |
| C17 | 2.25% w/w/anionic surfactant (AOS) 0.75% w/w sodium chloride | <100 |
| E26 | 3.75% w/w/zwitterionic surfactant | 23410 |
| C18 | 3.75% w/w/anionic surfactant (AOS) 0.75% w/w sodium chloride | <100 |
| E27 | 3.75% w/w/zwitterionic surfactant | 35320 |
| C19 | 7.35% w/w/anionic surfactant (AOS) 0.75% w/w sodium chloride | <100 |
| E28 | 3.75% w/w/zwitterionic surfactant | 225800 |
| C20 | 3.75% w/w/anionic surfactant (AOS) 0% w/w sodium chloride | <100 |
| E29 | 3.75% w/w/zwitterionic surfactant | 3159 |
| C21 | 3.75% w/w/anionic surfactant (AOS) 0.75% w/w sodium chloride | <100 |
| E30 | 3.75% w/w/zwitterionic surfactant | 487 |
| C22 | 3.75% w/w/anionic surfactant (AOS) 1.25% w/w sodium chloride | <100 |

Inventive Examples E31-E36 and Comparative Examples C23-C28

Preparation and Measurement of Certain Compositions of the Invention with SCG as the Anionic Surfactant and Comparative Compositions Compositions E31-E36 and Comparative Compositions C23-C28 were made in accord with the procedure described for Compositions E5-E18 and Comparative Compositions C5-C14, except that Plantapon ACG H2 was used as the anionic surfactant instead of Rhodapex ES-2K and while preparing the stock solution with the anionic surfactant, Plantapon ACG H2, the batch was heated to 45° C. and kept at 45° C. until the stock solution was added to the Compositions E31-E36 and Comparative Compositions C23-C28, as shown in Tables 11 and 12.

The Zero Shear Viscosity was measured in accord with the Zero Shear Viscosity Test as described herein. The results are shown in Table 13. As a result, applicants discovered that zwitterionic ester ammonioalkanoate surfactants are compatible with sodium cocoyl glutamate and have the tendency to build desired viscosity in such compositions, whereas zwitterionic alkylamidoamine betaine surfactants are not compatible, i.e. precipitation and phase separation occur when combined with sodium cocoyl glutamate at a pH of around 4.5.

TABLE 11

| Material | Trade Name | Activity (%) | E31 wt. % | E32 wt. % | E33 wt. % | C23 wt. % | C24 wt. % | C25 wt. % |
|---|---|---|---|---|---|---|---|---|
| Weight ratio zwitterionic/amphoteric to anionic surfactant (active to active) | | | 1.67 | 0.79 | 0.51 | 1.67 | 0.79 | 0.51 |
| Zwitterionic (weight % active) | | | | | | | | |
| E4 | N/A | 29.7 | 3.75 | 3.75 | 3.75 | | | |
| C1 | Tego betaine L7V | 30 | | | | 3.75 | 3.75 | 3.75 |
| Anionic (weight % active) | | | | | | | | |
| Sodium Cocoyl Glutamate | Plantapon ACG H2 | 42.7 | 2.25 | 4.75 | 7.35 | 2.25 | 4.75 | 7.35 |
| Organic acids | | | | | | | | |
| Sodium Benzoate | Sodium Benzoate, NF, FCC | 100 | 0.50 | 0.50 | 0.50 | 0.50 | 0.50 | 0.50 |
| Citric Acid | Citric Acid solution | 20 | Q.S. to pH 4.5 | Q.S. to pH 4.5 | Q.S. to pH 4.5 | Q.S. to pH 4.5 | Q.S. to pH 4.5 | Q.S. to pH 4.5 |
| Other | | | | | | | | |
| Sodium Chloride | Sodium Chloride, USP | 100 | 1.25 | 1.25 | 1.25 | 1.25 | 1.25 | 1.25 |
| Water | Purified water, USP | 100 | Q.S. to 100% | Q.S. to 100% | Q.S. to 100% | Q.S. to 100% | Q.S. to 100% | Q.S. to 100% |

TABLE 12

| Material | Trade Name | Activity (%) | E34 wt. % | E35 wt. % | E36 wt. % | C26 wt. % | C27 wt. % | C28 wt. % |
|---|---|---|---|---|---|---|---|---|
| Weight ratio zwitterionic/amphoteric to anionic surfactant (active to active) | | | 1 | 1 | 1 | 1 | 1 | 1 |
| Zwitterionic (weight % active) | | | | | | | | |
| E2 | N/A | 88.6 | 3.75 | 3.75 | 3.75 | | | |
| C1 | Tego betaine L7V | 30 | | | | 3.75 | 3.75 | 3.75 |
| Anionic (weight % active) | | | | | | | | |
| Sodium Cocoyl Glutamate | Plantapon ACG H2 | 42.7 | 3.75 | 3.75 | 3.75 | 3.75 | 3.75 | 3.75 |
| Organic acids | | | | | | | | |
| Sodium Benzoate | Sodium Benzoate, NF, FCC | 100 | 0.50 | 0.50 | 0.50 | 0.50 | 0.50 | 0.50 |
| Citric Acid | Citric Acid solution | 20 | Q.S. to pH 4.5 | Q.S. to pH 4.5 | Q.S. to pH 4.5 | Q.S. to pH 4.5 | Q.S. to pH 4.5 | Q.S. to pH 4.5 |
| Other | | | | | | | | |
| Sodium Chloride | Sodium Chloride, USP | 100 | 0 | 0.75 | 1.25 | 0 | 0.75 | 1.25 |
| Water | Purified water, USP | 100 | Q.S. to 100% | Q.S. to 100% | Q.S. to 100% | Q.S. to 100% | Q.S. to 100% | Q.S. to 100% |

TABLE 13

| Example | Composition Information | Viscosity (Cps) |
|---|---|---|
| E31 | 3.75% w/w zwitterionic surfactant | 515 |
| C23 | 2.25% w/w anionic surfactant (SCG) | NA |
|  | 1.25% w/w sodium chloride |  |
| E32 | 3.75% w/w zwitterionic surfactant | 1990 |
| C24 | 4.75% w/w anionic surfactant (SCG) | NA |
|  | 1.25% w/w sodium chloride |  |
| E33 | 3.75% w/w zwitterionic surfactant | 2360 |
| C25 | 7.35% w/w anionic surfactant (SCG) | NA |
|  | 1.25% w/w sodium chloride |  |
| E34 | 3.75% w/w zwitterionic surfactant | 4575 |
| C26 | 3.75% w/w anionic surfactant (SCG) | NA |
|  | 0% w/w sodium chloride |  |
| E35 | 3.75% w/w zwitterionic surfactant | 4743 |
| C27 | 3.75% w/w anionic surfactant (SCG) | NA |
|  | 0.75% w/w sodium chloride |  |
| E36 | 3.75% w/w zwitterionic surfactant | 4000 |
| C28 | 3.75% w/w anionic surfactant (SCG) | NA |
|  | 1.25% w/w sodium chloride |  |

Inventive Examples E37-E42 and Comparative Examples C29-C34

Preparation and Measurement of Certain Compositions of the Invention with SM2S as the Anionic Surfactant and Comparative Compositions Compositions E37-E42 and Comparative Compositions C29-C34 were made in accord with the procedure described for Compositions E5-E18 and Comparative Compositions C5-C14, except that Alphastep PC-48 was used as the anionic surfactant instead of Rhodapex ES-2K, as shown in Tables 14 and 15.

The Zero Shear Viscosity was measured in accord with the Zero Shear Viscosity Test as described herein. The results are shown in Table 16. As a result and surprisingly, applicants discovered that zwitterionic ester ammonioalkanoate surfactants can build viscosity in compositions containing SM2S as the anionic surfactant, whereas zwitterionic alkylamidoamine betaine surfactants cannot.

TABLE 14

| Material | Trade Name | Activity (%) | E37 wt. % | E38 wt. % | E39 wt. % | C29 wt. % | C30 wt. % | C31 wt. % |
|---|---|---|---|---|---|---|---|---|
| Weight ratio zwitterionic/amphoteric to anionic surfactant (active to active) | | | 1.67 | 0.79 | 0.51 | 1.67 | 0.79 | 0.51 |
| Zwitterionic (weight % active) | | | | | | | | |
| E4 | N/A | 29.7 | 3.75 | 3.75 | 3.75 | | | |
| C1 | Tego betaine L7V | 30 | | | | 3.75 | 3.75 | 3.75 |
| Anionic (weight % active) | | | | | | | | |
| SM2S | Alphastep PC-48 | 37 | 2.25 | 4.75 | 7.35 | 2.25 | 4.75 | 7.35 |
| Organic acids | | | | | | | | |
| Sodium Benzoate | Sodium Benzoate, NF, FCC | 100 | 0.50 | 0.50 | 0.50 | 0.50 | 0.50 | 0.50 |
| Citric Acid | Citric Acid solution | 20 | Q.S. to pH 4.5 | Q.S. to pH 4.5 | Q.S. to pH 4.5 | Q.S. to pH 4.5 | Q.S. to pH 4.5 | Q.S. to pH 4.5 |
| Other | | | | | | | | |
| Sodium Chloride | Sodium Chloride, USP | 100 | 0 | 0 | 0 | 0 | 0 | 0 |
| Water | Purified water, USP | 100 | Q.S. to 100% | Q.S. to 100% | Q.S. to 100% | Q.S. to 100% | Q.S. to 100% | Q.S. to 100% |

TABLE 15

| Material | Trade Name | Activity (%) | E40 wt. % | E41 wt. % | E42 wt. % | C32 wt. % | C33 wt. % | C34 wt. % |
|---|---|---|---|---|---|---|---|---|
| Weight ratio zwitterionic/amphoteric to anionic surfactant (active to active) | | | 1 | 1 | 1 | 1 | 1 | 1 |
| Zwitterionic (weight % active) | | | | | | | | |
| E4 | N/A | 29.7 | 3.75 | 3.75 | 3.75 | | | |
| C1 | Tego betaine L7V | 30 | | | | 3.75 | 3.75 | 3.75 |
| Anionic (weight % active) | | | | | | | | |
| SM2S | Alphastep PC-48 | 37 | 4.75 | 4.75 | 4.75 | 4.75 | 4.75 | 4.75 |
| Organic acids | | | | | | | | |
| Sodium Benzoate | Sodium Benzoate, NF, FCC | 100 | 0.50 | 0.50 | 0.50 | 0.50 | 0.50 | 0.50 |
| Citric Acid | Citric Acid solution | 20 | Q.S. to pH 4.5 | Q.S. to pH 4.5 | Q.S. to pH 4.5 | Q.S. to pH 4.5 | Q.S. to pH 4.5 | Q.S. to pH 4.5 |
| Other | | | | | | | | |
| Sodium Chloride | Sodium Chloride, USP | 100 | 0 | 0.75 | 1.25 | 0 | 0.75 | 1.25 |
| Water | Purified water, USP | 100 | Q.S. to 100% | Q.S. to 100% | Q.S. to 100% | Q.S. to 100% | Q.S. to 100% | Q.S. to 100% |

TABLE 16

| Example | Composition Information | Viscosity (cps) |
|---|---|---|
| E37 | 3.75% w/w/zwitterionic surfactant | 7216 |
| C29 | 2.25% w/w/anionic surfactant (SM2S) 0% w/w sodium chloride | <100 |
| E38 | 3.75% w/w/zwitterionic surfactant | 5737 |
| C30 | 4.75% w/w/anionic surfactant (SM2S) 0% w/w sodium chloride | <100 |
| E39 | 3.75% w/w/zwitterionic surfactant | NA |
| C31 | 7.35% w/w/anionic surfactant (SM2S) 0% w/w sodium chloride | <100 |
| E40 | 3.75% w/w/zwitterionic surfactant | 5737 |
| C32 | 4.75% w/w/anionic surfactant (SM2S) 0% w/w sodium chloride | <100 |
| E41 | 3.75% w/w/zwitterionic surfactant | 2033 |
| C33 | 4.75% w/w/anionic surfactant (SM2S) 0.75% w/w sodium chloride | <100 |
| E42 | 3.75% w/w/zwitterionic surfactant | 1376 |
| C34 | 4.75% w/w/anionic surfactant (SM2S) 1.25% w/w sodium chloride | <100 |

Inventive Examples E43-E50 and Comparative Examples C35-C42

Preparation and Measurement of Certain Compositions of the Invention with and without PS-111 as an Anionic Surfactant and Comparative Compositions Compositions E43-E50 and Comparative Compositions C35-C42 were made in accord with the following procedure: Unless otherwise indicated, all materials were added in amounts such that the compositions contain resulting weight percent amounts of active as indicated for each composition in Tables 17 and 19. For example, 3.75% w/w active of cocamidopropyl betaine (as given in table 17, C35) corresponds to 12.5% w/w Tego betaine L7V, which has an activity of 30% w/w; 3.75% w/w/30% w/w=12.5% w/w.

Compositions E43-E50 and Comparative Compositions C35-C42 were made as follows: To an appropriately sized vessel equipped with a hotplate and overhead mechanical stirrer, the required amount of DI water, zwitterionic surfactant, anionic surfactant, and sodium benzoate are added and mixed at 200-350 rpm until the mixture is homogeneous; for E2 at 50° C., for E4 and C1 at room temperature. Then, citric acid (20% w/w solution in DI water) is added at room temperature to adjust to the desired pH value 4.4-4.6. Then, Structure PS-111 and Sodium chloride are added and mixed until the mixture is homogeneous. Water was added in q.s. to 100 wt %, and the batch is allowed to mix until uniform before being discharged to an appropriate storage vessel. Tables 17 and 19 list such compositions.

The Zero Shear Viscosity and Max. Foam Volume were measured in accord with the Zero Shear Viscosity Test and Formulation Foam Test, respectively, as described herein. The results are shown in Table 18 and 20. As a result and surprisingly, applicants discovered that zwitterionic ester ammonioalkanoate surfactants can not only build viscosity in compositions containing AOS and/or SM2S as the anionic surfactant, but that such compositions also exhibit better foamability compared to compositions with zwitterionic alkylamidoamine betaine surfactants.

TABLE 17

| Material | Trade Name | Activity (%) | E43 wt. % | E44 wt. % | E45 wt. % | E46 wt. % | C35 wt. % | C36 wt. % | C37 wt. % | C38 wt. % |
|---|---|---|---|---|---|---|---|---|---|---|
| Zwitterionic (weight % active) | | | | | | | | | | |
| E2 | N/A | 88.6 | 3.75 | 3.75 | 3.75 | 3.75 | | | | |
| C1 | Tego betaine L7V | 30 | | | | | 3.75 | 3.75 | 3.75 | 3.75 |
| Anionic (weight % active) | | | | | | | | | | |
| AOS | Bioterge AS-40 | 39 | 3.75 | 3.75 | | | 3.75 | 3.75 | | |
| SM2S | Alphastep PC-48 | 37 | | | 2.25 | 2.25 | | | 2.25 | 2.25 |
| Sodium hydrolyzed potato starch dodecenyl-succinate | Structure PS-111 | 94 | | 3 | | 3 | | 3 | | 3 |
| Organic acids | | | | | | | | | | |
| Sodium Benzoate | Sodium Benzoate, NF, FCC | 100 | 0.50 | 0.50 | 0.50 | 0.50 | 0.50 | 0.50 | 0.50 | 0.50 |
| Citric Acid | Citric Acid solution | 20 | Q.S. to pH 4.5 | Q.S. to pH 4.5 | Q.S. to pH 4.5 | Q.S. to pH 4.5 | Q.S. to pH 4.5 | Q.S. to pH 4.5 | Q.S. to pH 4.5 | Q.S. to pH 4.5 |
| Other | | | | | | | | | | |
| Sodium Chloride | Sodium Chloride, USP | 100 | 0.6 | 0.6 | 0.2 | 0.2 | 0.6 | 0.6 | 0.2 | 0.2 |
| Water | Purified water, USP | 100 | Q.S. to 100% | Q.S. to 100% | Q.S. to 100% | Q.S. to 100% | Q.S. to 100% | Q.S. to 100% | Q.S. to 100% | Q.S. to 100% |

TABLE 18

| Example | Composition Information | Viscosity (cps) | Foam Volume (ml) |
|---|---|---|---|
| E43 | 3.75% w/w/zwitterionic surfactant | 435000 | 340 |
| C35 | 3.75% w/w/anionic surfactant (AOS) | 34 | 269 |
|  | 0% w/w Structure PS-111 |  |  |
|  | 0.6% w/w sodium chloride |  |  |
| E44 | 3.75% w/w/zwitterionic surfactant | 46000 | 360 |
| C36 | 3.75% w/w/anionic surfactant (AOS) | 75 | 280 |
|  | 3% w/w Structure PS-111 |  |  |
|  | 0.6% w/w sodium chloride |  |  |
| E45 | 3.75% w/w/zwitterionic surfactant | 32000 | 245 |
| C37 | 2.25% w/w/anionic surfactant (SM2S) | 4 | 154 |
|  | 0% w/w Structure PS-111 |  |  |
|  | 0.2% w/w sodium chloride |  |  |
| E46 | 3.75% w/w/zwitterionic surfactant | 2500 | 330 |
| C38 | 2.25% w/w/anionic surfactant (SM2S) | 30 | 280 |
|  | 3% w/w Structure PS-111 |  |  |
|  | 0.2% w/w sodium chloride |  |  |

TABLE 19

| Material | Trade Name | Activity (%) | E47 wt. % | E48 wt. % | E49 wt. % | E50 wt. % | C39 wt. % | C40 wt. % | C41 wt. % | C42 wt. % |
|---|---|---|---|---|---|---|---|---|---|---|
| Zwitterionic (weight % active) | | | | | | | | | | |
| E4 | N/A | 29.7 | 3.75 | 3.75 | 3.75 | 3.75 | | | | |
| C1 | Tego betaine L7V | 30 | | | | | 3.75 | 3.75 | 3.75 | 3.75 |
| Anionic (weight % active) | | | | | | | | | | |
| AOS | Bioterge AS 40-CP | 39 | 5.75 | 5.75 | | | 5.75 | 5.75 | | |
| SM2S | Alphastep PC-48 | 37 | | | 3.74 | 3.74 | | | 3.74 | 3.74 |
| Sodium hydrolyzed potato starch dodecenyl-succinate | Structure PS-111 | 94 | | 3 | | 3 | | 3 | | 3 |
| Organic acids | | | | | | | | | | |
| Sodium Benzoate | Sodium Benzoate, NF, FCC | 100 | 0.50 | 0.50 | 0.50 | 0.50 | 0.50 | 0.50 | 0.50 | 0.50 |
| Citric Acid | Citric Acid solution | 20 | Q.S. to pH 4.5 | Q.S. to pH 4.5 | Q.S. to pH 4.5 | Q.S. to pH 4.5 | Q.S. to pH 4.5 | Q.S. to pH 4.5 | Q.S. to pH 4.5 | Q.S. to pH 4.5 |
| Other | | | | | | | | | | |
| Sodium Chloride | Sodium Chloride, USP | 100 | 1.45 | 1.45 | 0.2 | 0.2 | 1.45 | 1.45 | 0.2 | 0.2 |
| Water | Purified water, USP | 100 | Q.S. to 100% | Q.S. to 100% | Q.S. to 100% | Q.S. to 100% | Q.S. to 100% | Q.S. to 100% | Q.S. to 100% | Q.S. to 100% |

TABLE 20

| Example | Composition Information | Viscosity (Cps) | Foam Volume (ml) |
|---|---|---|---|
| E47 | 3.75% w/w/zwitterionic surfactant | 75000 | 435 |
| C39 | 5.75% w/w/anionic surfactant (AOS) | 175 | 307 |
|  | 0% w/w Structure PS-111 |  |  |
|  | 1.45% w/w sodium chloride |  |  |
| E48 | 3.75% w/w/zwitterionic surfactant | 43000 | 425 |
| C40 | 5.75% w/w/anionic surfactant (AOS) | 348 | 353 |
|  | 3% w/w Structure PS-111 |  |  |
|  | 1.45% w/w sodium chloride |  |  |
| E49 | 3.75% w/w/zwitterionic surfactant | 2300 | 330 |
| C41 | 3.74% w/w/anionic surfactant (SM2S) | 1 | 154 |
|  | 0% w/w Structure PS-111 |  |  |
|  | 0.2% w/w sodium chloride |  |  |
| E50 | 3.75% w/w/zwitterionic surfactant | 1300 | 365 |
| C42 | 3.74% w/w/anionic surfactant (SM2S) | 4 | 257 |
|  | 3% w/w Structure PS-111 |  |  |
|  | 0.2% w/w sodium chloride |  |  |

Inventive Examples E51-E52 and Comparative Example C43

Preparation and Measurement of Certain Compositions of the Invention with Nonionic Surfactants and Conditioning Polymer and Comparative Compositions Compositions E51-E52 and Comparative Composition C43 were made in accord with the following procedure: Unless otherwise indicated, all materials were added in amounts such that the compositions contain resulting weight percent amounts of active as indicated for each composition in Table 21. For example, 3.75% w/w active of cocamidopropyl betaine (as given in table 21, C43) corresponds to 12.5% w/w Tego betaine L7V, which has an activity of 30% w/w; 3.75% w/w/30% w/w=12.5% w/w. Compositions E51-E52 and Comparative Composition C43 were made as follows: To an appropriately sized vessel equipped with a hotplate and overhead mechanical stirrer, 90% of the required amount of DI water, all PEG-80 Sorbitan Laurate, and Polyquaternium-10 dispersed in glycerin were added and the batch was heated to 80-85° C. under mixing. When temperature reached 55° C., PEG-150 Distearate was added and mixed until the batch reached 80-85° C. and was uniform. The heat was turned off and Rhodapex EST-65 (STDES) was added, mixed until uniform. Then, the zwitterionic surfactant was added and the batch was mixed until the mixture was homogeneous. Versene 100 XL, sodium benzoate, and Euxyl PE 9010 were added and mixed until the mixture was homogeneous. When the batch had cooled below 50° C., citric acid (20% w/w solution in DI water) was added to adjust to the desired pH value 5.2-5.4. Water was added in q.s. to 100 wt %, and the batch was allowed to mix until uniform before being discharged to an appropriate storage vessel. Table 21 lists such compositions.

The Zero Shear Viscosity and Max. Foam Volume were measured in accord with the Zero Shear Viscosity Test and Formulation Foam Test, respectively, as described herein. The results are shown in Table 22. As a result, applicants discovered that zwitterionic ester ammonioalkanoate surfactants have the tendency to build higher viscosity in comparison to zwitterionic alkylamidoamine betaine surfactants in compositions containing anionic surfactant and several other formulation ingredients, like non-ionic surfactants (e.g. PEG80 sorbitan laurate), chelating agent, glycerin, a cationic conditioning polymer (Polyquaternium-10) and different preservatives. Such compositions also exhibit equivalent or better foamability in comparison to the equivalent compositions containing zwitterionic alkylamidoamine betaine surfactants.

TABLE 21

| Material | Trade Name | Activity (%) | E51 wt. % | E52 wt. % | C43 wt. % |
|---|---|---|---|---|---|
| E2 | N/A | 88.6 | 3.2 | | |
| E4 | N/A | 29.7 | | 3.2 | |
| C4 | Tego betaine F50 | 38 | | | 3.2 |
| Sodium Trideceth Sulfate | Rhodapex EST-65 | 65 | 2.41 | 2.41 | 2.41 |
| PEG-80 Sorbitan Laurate | Atlas G-4280 | 72 | 3.2 | 3.2 | 3.2 |
| PEG-150 Distearate | Exthox PEG-6000 DS Special | 100 | 1.1 | 1.1 | 1.1 |
| Polyquaternium-10 | Ucare JR-400 | 100 | 0.14 | 0.14 | 0.14 |
| Glycerin | Emery 917 | 99.7 | 0.5 | 0.5 | 0.5 |
| Tetrasodium EDTA | Versene 100XL | 38 | 0.2 | 0.2 | 0.2 |
| Sodium Benzoate | Sodium Benzoate, NF, FCC | 100 | 0.30 | 0.30 | 0.30 |

TABLE 21-continued

| Material | Trade Name | Activity (%) | E51 wt. % | E52 wt. % | C43 wt. % |
|---|---|---|---|---|---|
| Phenoxy ethanol and ethylhexylglycerin | Euxyl PE 9010 | 100 | 0.7 | 0.7 | 0.7 |
| Citric Acid | Citric Acid solution | 20 | Q.S. to pH 4.5 | Q.S. to pH 4.5 | Q.S. to pH 4.5 |
| Water | Purified water, USP | 100 | Q.S. to 100% | Q.S. to 100% | Q.S. to 100% |

TABLE 22

| Example | Viscosity (cps) | Foam Volume (ml)* |
|---|---|---|
| E51 | 11200 | 217 |
| E52 | 10400 | 354 |
| C43 | 2600 | 210 |

*Tested at 0.5 wt % in simulated hard water.

Inventive Examples E53-E60 and Comparative Examples C44-C47

Preparation and Measurement of Certain Compositions of the Invention with PS-111 and Nonionic Surfactants and Comparative Compositions Compositions E53-E60 and Comparative Compositions C44-C47 were made in accord with the following procedure: Unless otherwise indicated, all materials were added in amounts such that the compositions contain resulting weight percent amounts of active as indicated for each composition in Tables 23 and 24. For example, 3.75% w/w active of cocamidopropyl betaine (as given in table 23, C44) corresponds to 12.5% w/w Tego betaine L7V, which has an activity of 30% w/w; 3.75% w/w/30% w/w=12.5% w/w. Compositions E53-E60 and Comparative Compositions C44-C47 were made as follows: To an appropriately sized vessel equipped with a hotplate and overhead mechanical stirrer, 90% of the required amount of DI water, zwitterionic, anionic surfactants (Rhodapex ES-2K and, Structure PS-111), and the Polyaldo surfactant were added and the batch was mixed at 200-350 rpm until the mixture was homogeneous. Citric acid (20% w/w solution in DI water) was added to adjust to the desired pH value 4.4-4.6. Sodium benzoate and sodium chloride were added. Water was added in q.s. to 100 wt %, and the batch is allowed to mix until uniform before being discharged to an appropriate storage vessel. Tables 23 and 24 list such compositions.

The Zero Shear Viscosity and Max. Foam Volume were measured in accord with the Zero Shear Viscosity Test and Formulation Foam Test, respectively, as described herein. The results are shown in Table 25. As a result, applicants discovered that zwitterionic ester ammonioalkanoate surfactants have the tendency to build higher viscosity in comparison to zwitterionic alkylamidoamine betaine surfactants in compositions containing anionic surfactants and several other formulation ingredients, like polyglycerol ester surfactants. Such compositions also exhibit equivalent or better foamability in comparison to the equivalent compositions containing zwitterionic alkylamidoamine betaine surfactants.

TABLE 23

| Material | Trade Name | Activity (%) | E53 wt. % | E54 wt. % | E55 wt. % | E56 wt. % | C44 wt. % | C45 wt. % |
|---|---|---|---|---|---|---|---|---|
| Weight ratio zwitterionic/amphoteric to anionic surfactant (active to active) | | | 0.87 | 0.87 | 0.87 | 0.87 | 0.87 | 0.87 |
| Zwitterionic (weight % active) | | | | | | | | |
| E1 | N/A | 28.1 | 3.75 | 3.75 | | | | |
| E4 | N/A | 29.7 | | | 3.75 | 3.75 | | |
| C1 | Tego betaine L7V | 30 | | | | | 3.75 | 3.75 |
| Anionic (weight % active) | | | | | | | | |
| Sodium laureth-2 Sulfate | Rhodapex ES-2K | 26 | 3.3 | 3.3 | 3.3 | 3.3 | 3.3 | 3.3 |
| PS-111 | Structure PS-111 | 94 | 1 | 1 | 1 | 1 | 1 | 1 |
| Nonionic (weight % active) | | | | | | | | |
| | Polyaldo 10-1-L | 100 | 1 | | 1 | | 1 | |
| | Polyaldo 10-1-O | 100 | | 1 | | 1 | | 1 |
| Organic acids | | | | | | | | |
| Sodium Benzoate | Sodium Benzoate, NF, FCC | 100 | 0.50 | 0.50 | 0.50 | 0.50 | 0.50 | 0.50 |
| Citric Acid | Citric Acid solution | 20 | Q.S. to pH 4.5 | Q.S. to pH 4.5 | Q.S. to pH 4.5 | Q.S. to pH 4.5 | Q.S. to pH 4.5 | Q.S. to pH 4.5 |
| Other | | | | | | | | |
| Sodium Chloride | Sodium Chloride, USP | 100 | 0.47 | 0.47 | 0.47 | 0.47 | 0.47 | 0.47 |
| Water | Purified water, USP | 100 | Q.S. to 100% | Q.S. to 100% | Q.S. to 100% | Q.S. to 100% | Q.S. to 100% | Q.S. to 100% |

TABLE 24

| Material | Trade Name | Activity (%) | E57 wt. % | E58 wt. % | E59 wt. % | E60 wt. % | C46 wt. % | C47 wt. % |
|---|---|---|---|---|---|---|---|---|
| Weight ratio zwitterionic/amphoteric to anionic surfactant (active to active) | | | 0.51 | 0.51 | 0.51 | 0.51 | 0.51 | 0.51 |
| Zwitterionic (weight % active) | | | | | | | | |
| E1 | N/A | | 3.75 | 3.75 | | | | |
| E4 | N/A | 29.7 | | | 3.75 | 3.75 | | |
| C1 | Tego betaine L7V | 30 | | | | | 3.75 | 3.75 |
| Anionic (weight % active) | | | | | | | | |
| Sodium laureth-2 Sulfate | Rhodapex ES-2K | 26 | 6.3 | 6.3 | 6.3 | 6.3 | 6.3 | 6.3 |
| PS-111 | | | 1 | 1 | 1 | 1 | 1 | 1 |
| Nonionic (weight % active) | | | | | | | | |
| | Polyaldo 10-1-L | | 1 | | 1 | | 1 | |
| | Polyaldo 10-1-O | | | 1 | | 1 | | 1 |
| Organic acids | | | | | | | | |
| Sodium Benzoate | Sodium Benzoate, NF, FCC | 100 | 0.50 | 0.50 | 0.50 | 0.50 | 0.50 | 0.50 |
| Citric Acid | Citric Acid solution | 20 | Q.S. to pH 4.5 | Q.S. to pH 4.5 | Q.S. to pH 4.5 | Q.S. to pH 4.5 | Q.S. to pH 4.5 | Q.S. to pH 4.5 |
| Other | | | | | | | | |
| Sodium Chloride | Sodium Chloride, USP | 100 | 1.22 | 1.22 | 1.22 | 1.22 | 1.22 | 1.22 |
| Water | Purified water, USP | 100 | Q.S. to 100% | Q.S. to 100% | Q.S. to 100% | Q.S. to 100% | Q.S. to 100% | Q.S. to 100% |

TABLE 25

| Example | Viscosity (Cps) | Foam Volume (ml) |
|---|---|---|
| E53 | 10400 | 280 |
| E55 | 7000 | 320 |
| C44 | 457 | 279 |
| E54 | 41000 | 270 |
| E56 | 23000 | 300 |
| C45 | 1685 | 280 |
| E57 | 34000 | 320 |
| E59 | 26000 | 390 |
| C46 | 25240 | 390 |
| E58 | 73000 | 380 |
| E60 | 57000 | 390 |
| C47 | 16490 | 359 |

Inventive Example E61 and Comparative Example C48

Preparation and Measurement of Certain Compositions of the Invention Equivalent to Commercial Formulations Composition E61 and Comparative Composition C48 were made in accord with the following procedure: All materials were added in amounts as indicated for each composition in Tables 26. For example, 16.4% w/w E4 (as given in table 26, E61) had been added, which corresponds to an activity of 4.87% w/w active of the 3-((3-(lauroyloxy)butyl)dimethylammonio)-2-hydroxypropanesulfonate; 16.4% w/w*29.7% w/w=4.87% w/w. Compositions E61 and Comparative Composition C48 were made as follows: To an appropriately sized vessel equipped with a hotplate and overhead mechanical stirrer, 90% of the required amount of DI water was added, stirred at 200-350 rpm and heated to 35-40° C. The Carbopol ETD2020 was sifted slowly into the vortex. The mixture was stirred until the polymer was fully dispersed. The pH was adjusted to 6.0-6.2 by adding 50% w/w NaOH in water. The Structure PS-111 was sifted slowly into the mix under stirring. The mixture was stirred until homogenous. The Rhodapex ES-2K, the zwitterionic surfactant and the sodium benzoate were added to the mixture. The mixture was stirred until homogeneous. The Natural Extract Scent was added and the mixture homogenized. The Jaguar C17 was dispersed into glycerin in a separate vessel. This dispersion was added slowly into the mixture under stirring. The Euperlan PK3000 AM was added to the mixture under stirring. The pH was adjusted to pH 4.5-4.9 using citric acid. Water was added in q.s. to 100 wt %, and the batch is allowed to mix until uniform before being discharged to an appropriate storage vessel. Table 26 lists the compositions.

The Zero Shear Viscosity and Max. Foam Volume were measured in accord with the Zero Shear Viscosity Test and Formulation Foam Test, respectively, as described herein. The results are shown in Table 27. As a result, applicants discovered that zwitterionic ester ammonioalkanoate surfactants have the tendency to build higher viscosity in comparison to zwitterionic alkylamidoamine betaine surfactants in compositions containing anionic surfactants and several other formulation ingredients, like cationic guar (conditioning polymer), hydrophobically modified acrylate crosspolymer (rheology polymer), glycol distearate (pearlizing agent) and fragrance. Such compositions also exhibit equivalent or better foamability in comparison to the equivalent compositions containing zwitterionic alkylamidoamine betaine surfactants. Applicants note the comparative examples are normalized to the same surfactant concentrations (% w/w active) as corresponding Inventive Example (C48 corresponds to E61).

TABLE 26

| Material | Trade Name | Activity (%) | E61 wt. % of Material as-is | C48 wt. % of Material as-is |
|---|---|---|---|---|
| E4 | N/A | 29.7 | 16.4 | |
| C4 | Tego betaine F50 | 38 | | 12.4 |
| Sodium laureth-2 Sulfate | Rhodapex ES-2K | 26 | 17.5 | 17.5 |
| PS-111 | Structure PS-111 | 100 | 2.5 | 2.5 |
| Acrylates/C10-30 Alkyl Acrylate Crosspolymer | Carbopol ETD2020 | 100 | 0.1 | 0.1 |
| Guar Hydroxypropyltrimonium Chloride | Jaguar C17 | 100 | 0.5 | 0.5 |
| Glycerin | Glycerin 99.7% Min USP Kosher | 99.7 | 1 | 1 |
| Glycol Distearate (and) Laureth-4 (and) Cocamidopropyl Betaine | Euperlan PK3000 AM | | 2.5 | 2.5 |
| | Dissolvine GL-47-S | 100 | 0.63 | 0.63 |
| Fragrance | Natural Extract 400-187 Part No. 06136 | 100 | 0.2 | 0.2 |
| Sodium Benzoate | Sodium Benzoate, NF, FCC | 100 | 0.50 | 0.50 |
| | Sodium Hydroxide Pellets NF/FCC Grade | 100 | Q.S. to pH 4.5 | Q.S. to pH 4.5 |
| Citric Acid | Citric Acid solution | 20 | Q.S. to pH 4.5 | Q.S. to pH 4.5 |
| Water | Purified water, USP | 100 | Q.S. to 100% | Q.S. to 100% |

TABLE 27

| Example | Viscosity (Cps) | Foam Volume (ml) |
|---|---|---|
| E61 | 139600 | 336 |
| C48 | 32110 | 323 |

Example E62 and Comparative Examples C49-050

Preparation and Measurement of Certain Compositions of the Invention Containing No Anionic Surfactant and Comparative Compositions Composition E62 and Comparative Compositions C49-050 were made in accord with the following procedure: All materials were added in amounts as indicated for each composition in Tables 28. For example, 7% w/w E4 (as given in table 28, E62) had been added, which corresponds to an activity of 2% w/w active of the 3-((3-(lauroyloxy)butyl)dimethylammonio)-2-hydroxypropanesulfonate; 7% w/w*29.7% w/w=2% w/w. Compositions E62 and Comparative Composition C49(50) were made as follows: To an appropriately sized vessel equipped with a hotplate and overhead mechanical stirrer, 90% of the required amount of DI water was added, stirred at 200-350 rpm. The Carbopol 1382 was sifted slowly into the vortex. The mixture was stirred until the polymer was fully dispersed. Sodium benzoate was added to the mixture and stirred until uniform. After adding glycerin, the batch was heated to 65-70° C. The pH was adjusted to 6.0-6.5 by adding 50% w/w NaOH in water. Plantaren 2000 N UP; Tegobetain L7V; Lamesoft PO 65; Polyaldo 10-1-L had been added one by one under stirring mixed until uniform. The heating was removed and the mixture was allowed to cool. At 55-60° C. Euxyl PE9010 was added. The pH was adjusted to 5.3-5.8. Water was added in q.s. to 100 wt %, and the batch is allowed to mix until uniform before being discharged to an appropriate storage vessel. Compositions prepared are listed in Table 28.

The Zero Shear Viscosity and Max. Foam Volume were measured in accord with the Zero Shear Viscosity Test and Formulation Foam Test, respectively, as described herein. The results are shown in Table 29. As a result, applicants discovered that zwitterionic ester ammonioalkanoate surfactants have the tendency to build higher viscosity in comparison to zwitterionic alkylamidoamine hydroxy sultaine (Miratine CBS) and betaine surfactants in compositions containing anionic surfactants and several other formulation ingredients. Such compositions also exhibit equivalent or better foamability in comparison to the equivalent compositions containing zwitterionic alkylamidoamine hydroxy sultaine and betaine surfactants. Applicants note the comparative examples are normalized to the same surfactant concentrations (% w/w active) as corresponding Inventive Examples (C49 and C50 correspond to E62).

TABLE 28

| Material | Trade Name | Activity (%) | E62 wt. % of Material as-is | C49 wt. % of Material as-is | C50 wt. % of Material as-is |
|---|---|---|---|---|---|
| E4 | N/A | 29.7 | 5.48 | | |
| C1 | Tego betaine L7V | 30 | | 7 | |
| C3 | Mirataine CBS | 42 | | | 4.55 |
| Coco-Glucoside; Glyceryl oleate | Lamesoft PO65 | 100 | 1 | 1 | 1 |
| Polyglyceryl-10 Laurate | POLYALDO 10-1-L | 100 | 1 | 1 | 1 |
| Decyl Glucoside | Plantaren 2000 N UP | | 14 | 14 | 14 |
| Acrylates/C10-30 Alkyl Acrylate Crosspolymer | Carbopol 1382 Polymer (CBP1004) | 100 | 0.6 | 0.61 | 0.61 |
| | Glycerin 99.7% Min USP Kosher | 100 | 1 | 1 | 1 |
| Phenoxyethanol; Ethylhexylglycerin | Euxyl PE 9010 | 100 | 0.9 | 0.9 | 0.9 |
| Sodium Benzoate | Sodium Benzoate, NF, FCC | 100 | 0.50 | 0.50 | 0.50 |
| | Sodium Hydroxide Pellets NF/FCC Grade | 100 | Q.S. to pH 5.5 | Q.S. to pH 5.5 | Q.S. to pH 5.5 |
| Citric Acid | Citric Acid solution | 20 | Q.S. to pH 5.5 | Q.S. to pH 5.5 | Q.S. to pH 5.5 |
| Water | Purified water, USP | 100 | Q.S. to 100% | Q.S. to 100% | Q.S. to 100% |

TABLE 29

| Example | Viscosity (Cps) | Foam Volume (ml) |
|---|---|---|
| E62 | 2035 | 268 |
| C49 | 2032 | 209 |
| C50 | 48350 | 222 |

Inventive Examples E63-E66 and Comparative Example $C_{JBS}$

Preparation and Mildness Measurement of Certain Compositions of the Invention and Comparative Compositions Compositions E63-E66 had been made according to the process described for E-5. Table 30 lists these compositions.

The Zero Shear Viscosity, EpiDerm™ $ET_{50}$ and EpiOcular™ $ET_{50}$ were measured in accord with the Zero Shear Viscosity Test, EpiDerm™ Test and EpiOcular™ Test, respectively, as described herein. The results are shown in Table 31. As a result, applicants discovered that zwitterionic ester ammonioalkanoate surfactants exhibit similar mildness in comparison to other zwitterionic surfactants like e.g. alkylamidoamine betaine surfactants in compositions containing anionic surfactants.

TABLE 30

| Material | Trade Name | Activity (%) | E63 | E64 | E65 | E66 |
|---|---|---|---|---|---|---|
| E1 | N/A | 29.7 | 3.75 | 3.75 | | |
| E3 | N/A | | | | 3.75 | 3.75 |
| Sodium laureth-2 Sulfate | Rhodapex ES-2K | 26 | 3.3 | 6.3 | 6.3 | 10.3 |
| Sodium Chloride | Sodium Chloride, USP | 100 | 0 | 0.75 | 0 | 0 |
| Sodium Benzoate | Sodium Benzoate, NF, FCC | 100 | 0.50 | 0.50 | 0.50 | 0.50 |
| | Sodium Hydroxide Pellets NF/FCC Grade | 100 | Q.S. to pH 4.5 | Q.S. to pH 4.5 | Q.S. to pH 4.5 | Q.S. to pH 4.5 |
| Citric Acid | Citric Acid solution | 20 | Q.S. to pH 4.5 | Q.S. to pH 4.5 | Q.S. to pH 4.5 | Q.S. to pH 4.5 |
| Water | Purified water, USP | 100 | Q.S. to 100% | Q.S. to 100% | Q.S. to 100% | Q.S. to 100% |

TABLE 31

| REMOVE VISCOSITY | | |
|---|---|---|
| Example | EpiDerm $ET_{50}$ (h) | EpiOcular $ET_{50}$ (h) |
| E63 | 13 | 5.0 |
| E64 | 11 | 1.9 |
| E65 | 9.3 | 2.3 |
| E66 | 7.5 | 1.5 |
| $C_{JBS}$ | 14.1 | 1.88 |

JBS is Johnson's Baby Shampoo - a commercially available benchmark composition.

What is claimed is:

1. A composition comprising a zwitterionic ester ammonioalkanoate surfactant according to Formula 1,

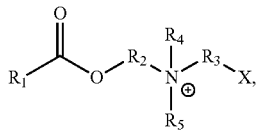

Formula 1 and an ingredient selected from the group consisting of a surfactant other than said zwitterionic ester ammonioalkanoate surfactant, emulsifiers, conditioning agents, emollients, moisturizers, humectants, thickeners, lubricants, chelating agents, fillers, binding agents, anti-oxidants, preservatives, active ingredients, fragrances, dyes, buffering agents, exfoliates, pH adjusters, inorganic salts, solvents, viscosity controlling agents and opacifying agents, wherein said zwitterionic ester ammonioalkanoate surfactant according to Formula 1 is a zwitterionic ester ammonioalkanoate sulfate surfactant, where R1 is a linear, branched, saturated or unsaturated C5 to C21 hydrophobe;
R2 is a linear, branched, or hydroxyalkyl group;
R3 is a linear, branched, or hydroxyalkyl group;
R4 is a linear, branched, or hydroxyalkyl group;
R5 is a linear, branched, or hydroxyalkyl group; and
X is —SO4-,
wherein said composition is substantially free of alkylamidoamine and aminoalkylamine.

2. The composition of claim 1 wherein said composition is free of alkylamidoamine and aminoalkylamine.

3. The composition of claim 1 wherein said surfactant other than said zwitterionic ester ammonioalkanoate surfactant according to Formula 1 is selected from the group consisting of anionic surfactant, cationic surfactant, non-ionic surfactant and zwitterionic surfactant.

4. The composition of claim 1 wherein said composition is substantially free of an anionic surfactant.

5. The composition of claim 1 wherein said composition is substantially free of a sulfated anionic surfactant.

6. The composition of claim 1 comprising from about 0.1% to about 30% of said zwitterionic ester ammonioalkanoate surfactant according to Formula 1.

7. The composition of claim 1 comprising from about 1% to about 10% of said zwitterionic ester ammonioalkanoate surfactant according to Formula 1.

8. The composition of claim 3 wherein said zwitterionic ester ammonioalkanoate surfactant according to Formula 1 and said surfactant other than said zwitterionic ester ammonioalkanoate surfactant according to Formula 1 are present at a weight ratio of from about 0.003 to about 300.

9. The composition of claim 3 wherein said zwitterionic ester ammonioalkanoate surfactant according to Formula 1 and said surfactant other than said zwitterionic ester ammonioalkanoate surfactant according to Formula 1 are present at a weight ratio of from about 0.1 to about 10.

10. The composition of claim 1 having a pH of from about 3 to about 9.

11. The composition of claim 1 comprising from about 0.05 to about 6 weight percent of said inorganic salt.

12. The composition of claim 1 wherein said composition is substantially free of a zwitterionic surfactant comprising an amide moiety.

13. The composition of claim 1 wherein said composition is free of a zwitterionic surfactant comprising an amide moiety.

* * * * *